United States Patent
Ali et al.

(10) Patent No.: US 8,612,055 B2
(45) Date of Patent: Dec. 17, 2013

(54) SYSTEM AND METHOD FOR DELIVERING A THERAPEUTIC AGENT ACCORDING TO DEFAULT INFUSION SCHEDULE

(75) Inventors: Irfan Z. Ali, Woodbury, MN (US); Steven M. Goetz, North Oaks, MN (US); David C. Ullestad, Maple Grove, MN (US); Emem D. Akpan, Coon Rapids, MN (US); Mark D. Salzwedel, Eden Prairie, MN (US); Jiaying Shen, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 841 days.

(21) Appl. No.: 12/761,801

(22) Filed: Apr. 16, 2010

(65) Prior Publication Data
US 2011/0257798 A1 Oct. 20, 2011

(51) Int. Cl.
*G01M 1/38* (2006.01)
*G05B 15/00* (2006.01)
*G05B 13/00* (2006.01)
*G05D 23/00* (2006.01)
*A61N 1/30* (2006.01)
*A61N 1/00* (2006.01)

(52) U.S. Cl.
USPC ............ 700/275; 700/282; 604/19; 604/30; 604/31; 604/65; 604/67

(58) Field of Classification Search
USPC ............ 700/275, 282; 604/19, 30–31, 65, 67
See application file for complete search history.

(56) References Cited

U.S. PATENT DOCUMENTS

| | | | | |
|---|---|---|---|---|
| 3,701,345 A | * | 10/1972 | Heilman et al. | 600/432 |
| 4,047,844 A | * | 9/1977 | Robinson | 417/3 |
| 4,308,866 A | * | 1/1982 | Jelliffe et al. | 604/31 |
| 4,715,852 A | * | 12/1987 | Reinicke et al. | 604/131 |
| 4,731,051 A | * | 3/1988 | Fischell | 604/67 |
| 5,181,910 A | * | 1/1993 | Scanlon | 604/67 |
| 5,472,614 A | | 12/1995 | Rossi | |
| 5,582,593 A | | 12/1996 | Hultman | |
| 5,712,795 A | * | 1/1998 | Layman et al. | 700/297 |
| 5,800,387 A | * | 9/1998 | Duffy et al. | 604/65 |
| 5,947,907 A | | 9/1999 | Duich | |
| 5,973,968 A | | 10/1999 | Schu et al. | |

(Continued)

FOREIGN PATENT DOCUMENTS

WO 2009103492 A1 8/2009

OTHER PUBLICATIONS

U.S. Appl. No. 61/165,467, filed Mar. 31, 2009; 33 pages; Wilinska et al; entire document.*

(Continued)

*Primary Examiner* — Ronald Hartman, Jr.
(74) *Attorney, Agent, or Firm* — Shumaker & Sieffert, P.A.

(57) ABSTRACT

A fluid delivery system comprises a pump configured to deliver a therapeutic agent to a patient, a memory storing a therapy program defining the delivery of the therapeutic agent to the patient by the pump and a default infusion schedule based on the therapy program, and a processor configured to control the pump to deliver the therapeutic agent to the patient according to the therapy program, to determine an error condition that prevents the pump from continuing to deliver therapy according to the therapy program, and, upon determination of the error condition, to control the pump to deliver the therapeutic agent to the patient according to the default infusion schedule.

53 Claims, 12 Drawing Sheets

(56) References Cited

U.S. PATENT DOCUMENTS

| | | | |
|---|---|---|---|
| 6,083,187 A * | 7/2000 | Nakayama et al. | 604/6.01 |
| 6,562,001 B2 | 5/2003 | Lebel et al. | |
| 6,571,128 B2 * | 5/2003 | Lebel et al. | 607/60 |
| 6,635,048 B1 | 10/2003 | Ullestad et al. | |
| 7,128,729 B2 * | 10/2006 | Duchon et al. | 604/154 |
| 7,505,869 B2 | 3/2009 | Hartlaub | |
| 7,913,496 B2 * | 3/2011 | Batenburg et al. | 62/50.6 |
| 8,057,492 B2 * | 11/2011 | Ortiz et al. | 606/151 |
| 8,262,617 B2 * | 9/2012 | Aeschlimann et al. | 604/151 |
| 8,323,245 B2 * | 12/2012 | List et al. | 604/131 |
| 2002/0156464 A1 | 10/2002 | Blischak et al. | |
| 2003/0217747 A1 | 11/2003 | Hickle et al. | |
| 2004/0220517 A1 * | 11/2004 | Starkweather et al. | 604/67 |
| 2005/0049656 A1 | 3/2005 | Petersen et al. | |
| 2005/0187515 A1 * | 8/2005 | Varrichio et al. | 604/67 |
| 2006/0173444 A1 * | 8/2006 | Choy et al. | 604/891.1 |
| 2008/0126969 A1 | 5/2008 | Blomquist | |
| 2009/0043290 A1 * | 2/2009 | Villegas et al. | 604/891.1 |
| 2009/0137956 A1 * | 5/2009 | Souter | 604/151 |
| 2010/0094261 A1 | 4/2010 | Bryant et al. | |
| 2011/0172633 A1 * | 7/2011 | Ali et al. | 604/500 |
| 2012/0157920 A1 * | 6/2012 | Flachbart et al. | 604/151 |

OTHER PUBLICATIONS

Zhang et al., "A hazard analysis for a generic insulin infusion pump," Journal of Diabetes Science and Technology, vol. 4, No. 2, pp. 263-283, Mar. 2010.

\* cited by examiner

SYSTEM AND METHOD FOR DELIVERING A THERAPEUTIC AGENT ACCORDING TO DEFAULT INFUSION SCHEDULE

TECHNICAL FIELD

The disclosure relates generally to implantable fluid delivery devices.

BACKGROUND

Implantable fluid delivery devices are used to treat a number of physiological, psychological, and emotional conditions, including chronic pain, tremor, Parkinson's disease, epilepsy, urinary or fecal incontinence, sexual dysfunction, obesity, spasticity, or gastroparesis. For some medical conditions, an implantable fluid delivery device provides the best, and in some cases the only, therapy to restore a patient to a more healthful condition.

An implantable fluid delivery device typically provides a patient with a programmable dosage or infusion of a drug or other therapeutic agent. The fluid delivery device typically includes a reservoir, a fill port, a pumping mechanism to pump the therapeutic agent from the reservoir, a catheter port to transport the therapeutic agent from the reservoir to a patient's anatomy, and electronics to control the pumping mechanism. The fluid delivery device also typically includes some form of fluid flow control in order to control or regulate the flow of the fluid therapeutic agent from the reservoir to the fluid delivery device outlet for delivery of the therapeutic agent to a desired location within the patient's body.

SUMMARY

In general, the disclosure relates to systems and methods of delivering a therapeutic fluid to a patient according to a default infusion schedule via an implantable fluid delivery device.

In one example, a fluid delivery system comprises a pump configured to deliver a therapeutic agent to a patient, a memory storing a therapy program defining the delivery of the therapeutic agent to the patient by the pump and a default infusion schedule based on the therapy program, and a processor configured to control the pump to deliver the therapeutic agent to the patient according to the therapy program, to determine an error condition that prevents the pump from continuing to deliver therapy according to the therapy program, and, upon determination of the error condition, to control the pump to deliver the therapeutic agent to the patient according to the default infusion schedule.

In another example, a method comprises determining a default infusion schedule based on a therapy program that defines delivery of a therapeutic agent to a patient by an implantable fluid delivery device, storing the default infusion schedule on a memory of the implantable fluid delivery device, determining if an error condition is present in the implantable fluid delivery device such that the device cannot continue delivering therapy according to the therapy program, and if the error condition is present, delivering the therapeutic agent according to the default infusion schedule.

In yet another example, a computer-readable medium includes instructions for causing a programmable processor to determine a default infusion schedule based on a therapy program that defines delivery of a therapeutic agent to a patient by an implantable fluid delivery device, store a default infusion schedule based on a therapy program that defines delivery of a therapeutic agent to a patient by an implantable fluid delivery device on the computer-readable medium, determine if an error condition is present in the implantable fluid delivery device such that the device cannot continue delivering therapy according to the therapy program, and if the error condition is present, deliver the therapeutic agent according to the default infusion schedule.

In another example, a fluid delivery system comprises means for delivering a therapeutic agent to a patient, means for storing a therapy program defining the delivery of the therapeutic agent to the patient by the means for delivering the therapeutic agent, means for storing a default infusion schedule based on the therapy program, and means for controlling the means for delivering the therapeutic agent to the patient, means for determining an error condition that prevents the means for delivering the therapeutic agent to the patient from continuing to deliver therapy according to the therapy program, wherein the means for controlling the means for delivering the therapeutic agent to the patient directs delivery of the therapeutic agent to the patient according to the default infusion schedule when the means for determining an error condition determines that the error condition is present.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
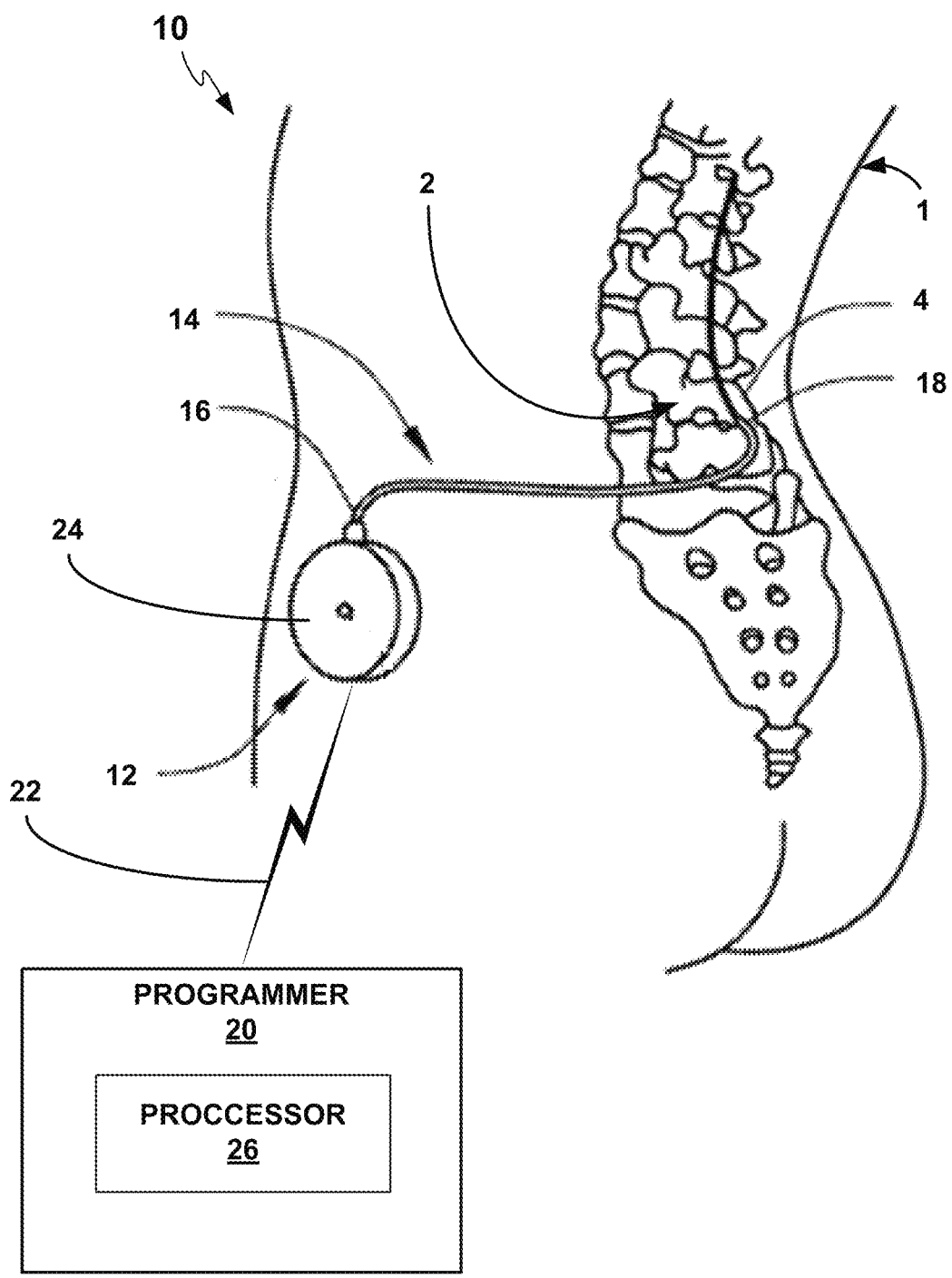
FIG. 1 is a conceptual diagram illustrating an example of a fluid delivery system, which includes an implantable fluid delivery device with a medical pump that is configured to deliver a therapeutic agent to a patient via a catheter.

The electronics of an implantable fluid delivery device may include a processor and other associated hardware to provide a prescribed dosage of a drug or other therapeutic agent under a set time schedule and under specified treatment parameters. The fluid delivery device may also include some form of memory, such as a Random Access Memory (RAM), Read-Only Memory (ROM), and/or a non-volatile memory such as EEPROM or Flash memory, for storing information regarding the control of the pumping mechanism, including treatment parameters such as a dosage infusion schedule. The fluid delivery device may also include hardware memory, such as hardware memory in an application specific integrated circuit (ASIC) or other integrated circuit (IC). Typically, treatment parameters, such as dosage rate and timing prescribed by a clinician are entered into the fluid delivery device using an external device commonly referred to as a physician, or clinician, programmer. The programmer may communicate with the fluid delivery device by telemetry in order to allow the clinician to program the fluid delivery device and to determine how the fluid delivery device is operating at any given time. The clinician can also use the programmer to change the treatment parameters, such as medication infusion rate or an infusion schedules.

Once the fluid delivery device is implanted in a patient, however, a number of complications may occur that affect the ability of the device to reliably deliver therapy to a patient. For example, the fluid delivery device memory that stores treatment parameters for drug delivery may become corrupted. Memory corruption can occur for several reasons. For example, memory corruption can be caused by a temporary drop in the battery voltage of the fluid delivery device power source, e.g., due to Electro-Magnetic Interference (EMI) or an internal power surge, software execution malfunctions, e.g., a bug or bit flip within the processor or memory, such as bit flip errors due to EMI or exposure to radiation or cosmic rays, that causes an erroneous program execution, or latent memory cell failures in which a memory cell loses its ability to hold programmed values over time. In some cases, if the memory is corrupted, the fluid delivery device may not be able to operate until the fluid delivery device is reprogrammed. This is undesirable because the patient will lose treatment therapy with the therapeutic agent until reprogramming is completed, which may result in the return of symptoms for the patient and, in some cases, may cause the patient to go into withdrawal.

In general, this disclosure is directed to techniques for providing an implantable fluid delivery device with a default infusion schedule that is determined based on a patient-specific and/or therapeutic agent-specific therapy program by which the device can continue to deliver the therapeutic agent to the patient when it is determined that an error condition exists that prevents continuing with the treatment infusion schedule defined by the therapy program. In this way, the fluid delivery device stores a therapy program defining delivery of a therapeutic agent to a patient under normal operating conditions onto a main memory on the fluid delivery device, as well as a backup default infusion schedule on a backup memory of the fluid delivery device that enables the fluid delivery device to continue delivering a therapeutic amount of the therapeutic agent to the patient even when an error condition would typically require the fluid delivery device to be shutdown.

An implantable fluid delivery device may be configured to deliver a therapeutic agent from a fluid reservoir to a patient according to a therapy program, which may, for example, specify a delivery rate of a fluid delivered to the patient by the fluid delivery device. As another example, a therapy program may adjust the delivery rate automatically based on physiological characteristics of a patient. In some instances, an external controller may be used to alter the therapy program as well as send and receive data relating to the operation of the fluid delivery device. In different examples, an external programmer may be operated by either one or both of a clinician and the patient.

FIG. 1 is a schematic diagram of an example system 10, including an implantable fluid delivery device, also referred to as an implantable medical device (IMD) 12, which is configured to deliver a therapeutic agent, such as a pharmaceutical agent, for example a drug, insulin, pain relieving agent, anti-inflammatory agent, gene therapy agent, or the like, to a target site 2 within a patient 1. In this manner, IMD 12 functions as an implantable fluid delivery device. The therapeutic agent is delivered via a catheter 14 that is coupled to IMD 12. Catheter 14 may comprise a plurality of catheter segments, or catheter 14 may be a unitary catheter. In the example shown in FIG. 1, target site 2 is proximate to spinal cord 4 of patient 1.

A proximal end 16 of catheter 14 is coupled to IMD 12 while a distal end 18 of catheter 14 is positioned proximate target site 2. System 10 may also include an external programmer 20 that communicates with IMD 12 as needed, such as to provide or retrieve therapy information or other treatment parameters associated with therapy delivery. For example, external programmer 20 may be configured to turn IMD 12 on or off, to deliver the initial therapy parameters for patient 1, to modify the therapy parameters, and so forth. In one example, external programmer 20 communicates with pump wirelessly 22, as shown in FIG. 1.

Although patient 1 is generally referred to as a human patient in the present disclosure, system 10 can be used with other mammalian or non-mammalian patients. IMD 12 may be employed to treat, manage or otherwise control various conditions or disorders of patient 1, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders.

IMD 12 may be configured to deliver one or more therapeutic agents, alone or in combination with other therapies, including, e.g., electrical stimulation. For example, in some cases, a medical pump may deliver one or more pain-relieving drugs to patients with chronic pain, insulin to a patient with diabetes, or other fluids to patients with different disorders. IMD 12 may be implanted in patient 1 for chronic or temporary therapy delivery.

IMD 12 includes an outer housing 24 that is constructed of a biocompatible material that resists corrosion and degradation from bodily fluids, such as titanium or biologically inert polymers. IMD 12 may be implanted within a subcutaneous pocket close to target 2. For example, as shown in FIG. 1, IMD 12 may be implanted within the abdomen of patient 1 close to the position along spinal cord 4 where target site 2 is located. In other examples, IMD 12 may be implanted within other suitable sites within patient 1, which may depend, for example, on where target site 2 is located within patient 1, and the ease of implanting IMD 12 within suitable locations near site target 2. IMD 12 may also be external to patient 1 with a percutaneous catheter connected between IMD 12 and the target delivery site 2 within the patient.

Catheter 14 may be coupled to IMD 12 either directly or with the aid of a catheter extension (not shown). In the example shown in FIG. 1, catheter 14 traverses from the implant site of IMD 12 to target site 2 proximate to spinal cord 4. Catheter 14 is positioned such that one or more fluid delivery outlets of catheter 14 are proximate to the one or more locations at target site 2 within patient 1. IMD 12 delivers a therapeutic agent to the target site 2 proximate to spinal cord 4 with the aid of catheter 14. For example, IMD 12 may be configured for intrathecal drug delivery into the intrathecal space or epidural space surrounding spinal cord 4.

In some examples, multiple catheters 14 may be coupled to IMD 12 to target the same or different tissue or nerve sites within patient 1. Thus, although a single catheter 14 is shown in FIG. 1, in other examples, system 10 may include multiple catheters or catheter 14 may define multiple lumens for delivering different therapeutic agents to patient 1 or for delivering a therapeutic agent to different tissue sites within patient 1. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

IMD 12 may deliver one or more therapeutic agents to patient 1 according to one or more therapy programs. Example therapeutic agents that IMD 12 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics. A therapy program, generally speaking, may set forth different therapy parameters, such as an infusion schedule specifying programmed doses, dose rates for the programmed doses, and specific times to deliver the programmed doses.

The therapy programs may be a part of a program group for therapy, wherein the group includes a plurality of constituent therapy programs and/or infusion schedules. In some examples, IMD 12 may be configured to deliver a therapeutic agent to patient 1 according to different therapy programs on a selective basis. IMD 12 may include a memory to store one or more therapy programs, instructions defining the extent to which patient 1 may adjust therapy parameters, switch between therapy programs, or undertake other therapy adjustments. Patient 1 may select and/or generate additional therapy programs for use by IMD 12 via external programmer 20 at any time during therapy or as designated by the clinician.

Programmer 20 is an external computing device that is configured to wirelessly communicate with IMD 12. For example, programmer 20 may be a clinician programmer that the clinician uses to communicate with IMD 12. Alternatively, programmer 20 may be a patient programmer that allows patient 1 to view and modify therapy parameters. The clinician programmer may include additional or alternative programming features, relative to the patient programmer. For example, more complex or sensitive tasks may only be allowed by the clinician programmer to prevent patient 1 from making undesired changes to the operation of IMD 12.

Programmer 20 may be a hand-held computing device that includes a display viewable by the user and a user input mechanism that can be used to provide input to programmer 20. For example, programmer 20 may include a processor 26, a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input. Processor 26 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 14, the position of catheter 14 within patient 1, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more therapy programs that define the therapy delivered by IMD 12 to patient 1. During a programming session, the clinician may determine one or more therapy programs that provide effective therapy to patient 1. Patient 1 may provide feedback to the clinician as to the efficacy of a specific therapy program being evaluated or desired modifications to the therapy program. Once the clinician has identified one or more programs that may be beneficial to patient 1, the patient may continue the evaluation process and determine which of these programs best alleviates the condition of or otherwise provides efficacious therapy to the patient. Programmer 20 may assist the clinician in the creation/identification of therapy programs by providing a methodical system of identifying potentially beneficial therapy parameters.

A therapy program may set forth a number of therapy parameters, e.g., different predetermined dosages of the therapeutic agent, the infusion rate of delivery of one or more of the therapeutic agent doses, a time interval between successive patient-initiated boluses (e.g., a lock-out interval), a maximum dose that may be delivered over a given time interval, and so forth. IMD 12 may include a feature that prevents dosing the therapeutic agent in a manner inconsistent with the therapy program. A dosage of a therapeutic agent may be expressed as an amount of the agent, e.g., measured in microliters, micrograms (mcg), or other volumetric or mass units provided to the patient over a particular time interval, e.g., per day or twenty-four hour period. This dosage amount may convey to the caregiver an indication of the probable efficacy of the therapeutic agent and the possibility of side effects of the agent. In general, a sufficient amount of the therapeutic agent should be administered in order to have a desired therapeutic effect, such as pain relief. However, the amount of the therapeutic agent administered to the patient may be limited to a maximum amount, such as a maximum daily dose, in order to avoid potential side effects. Program information specified by a user via programmer 20 may be used to control dosage amount, dosage rate, dosage time, maximum dose for a given time interval (e.g., daily), or other parameters associated with delivery of a drug or other therapeutic agent by IMD 12. The therapy program may also include a specific infusion schedule, wherein the infusion rate of the therapeutic agent for specific times and for specific time periods is set for patient 1. Examples of infusion schedules are described below with respect to FIGS. 5 and 6.

In some cases, programmer 20 may be configured for use by patient 1. When configured as a patient programmer, programmer 20 may have limited functionality in order to prevent patient 1 from altering critical functions or applications that may be detrimental to patient 1. In this manner, programmer 20 may only allow patient 1 to adjust certain therapy parameters or set an available range for a particular therapy parameter. In some cases, a patient programmer may permit the patient to control IMD 12 to deliver a supplemental, patient bolus or rate change, if permitted by the applicable therapy program administered by the IMD, e.g., if delivery of the patient bolus or rate change would not violate a lockout interval or maximum dosage limit. Programmer 20 may also provide an indication to patient 1 when therapy is being delivered, when IMD 12 needs to be refilled, or when the power source within programmer 20 or IMD 12 needs to be replaced or recharged.

Whether programmer 20 is configured for clinician or patient use, programmer 20 may communicate with IMD 12 or any other computing device via wireless communication link 22. Programmer 20, for example, may communicate via wireless communication link 22 with IMD 12 using radio frequency (RF) telemetry techniques. Programmer 20 may also communicate with another programmer or computing device via a wired or wireless connection using any of a variety of local wireless communication techniques, such as RF communication according to the 802.11 or Bluetooth specification sets, ZigBee communication standards, infrared (IR) communication according to the IRDA specification set, or other standard or proprietary telemetry protocols. Programmer 20 may also communicate with another programmer or computing device via exchange of removable media, such as magnetic or optical disks, or memory cards or sticks. Further, programmer 20 may communicate with IMD 12 and another programmer via remote telemetry techniques, or via a network, such as the internet, a local area network (LAN), a wide area network (WAN), a public switched telephone network (PSTN), or a cellular telephone network. IMD 12 may also communicate with another computing device, such as another programmer or an intermediate device such as a home monitoring device. IMD 12 may communicate with the other computing device wirelessly, similar to wireless communication 22 with programmer 20, or through a network, such as the internet, a local area network (LAN), a wide area network (WAN), a public switched telephone network (PSTN), or a cellular telephone network. In one example, IMD 12 is connected wirelessly to an interim network device that is connected to the network in order to communicate with the other computing device.

Figure 2:
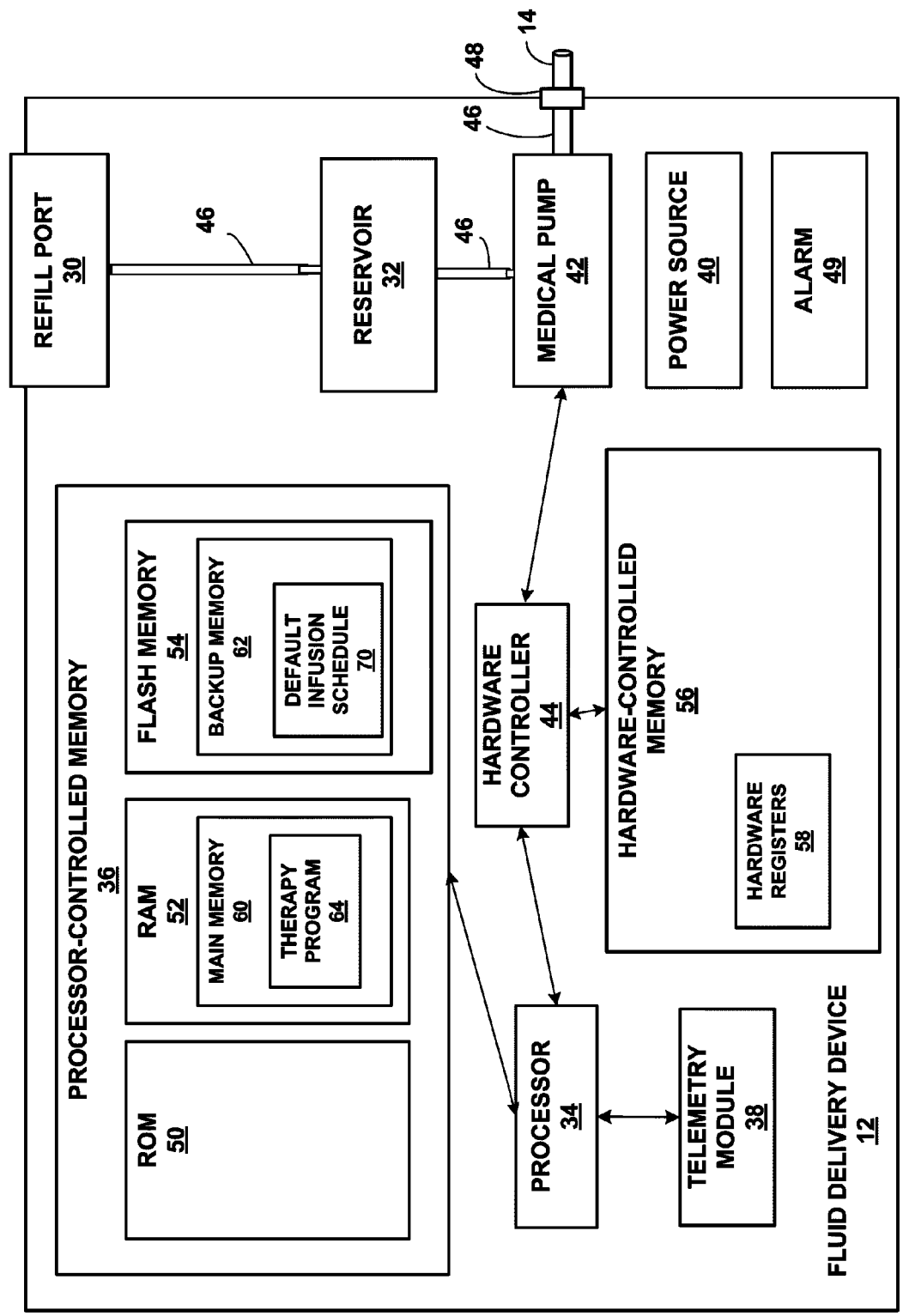
FIG. 2 is functional block diagram illustrating an example fluid delivery device with a medical pump.

FIG. 2 is a functional block diagram illustrating components of an example IMD 12, which may include a refill port 30, a reservoir 32, a processor 34, a memory, such as processor-controlled memory 36 and hardware-controlled memory 56, a telemetry module 38, a power source 40, a medical pump 42, a hardware controller 44, internal channels 46, and a catheter access port 48. Medical pump 42 may be any mechanism that delivers a therapeutic agent in some metered or other desired flow dosage to target site 2 within patient 1 from reservoir 32 via the catheter 14. Examples of medical pump 42 include a peristaltic pump that uses rollers or other actuation devices to move fluid along a pump tube and a piston pump where a piston pushes fluid from the pump. Refill port 30 may comprise a self-sealing injection port. The self-sealing injection port may include a self-sealing membrane to prevent loss of therapeutic agent delivered to reservoir 32 via refill port 30. After a delivery system, e.g., a hypodermic needle, penetrates the membrane of refill port 30, the membrane may seal shut when the needle is removed from refill port 30. Internal channels 46 includes one or more segments of tubing or a series of cavities that run from reservoir 32, around or through medical pump 42 to catheter access port 30. IMD 12 may also include an alarm 49 that is used to alert the patient of a condition within IMD 12, such as the detection of an error condition and/or the start of using default infusion schedule 70. As described in more detail below, default infusion schedule 70 provides a backup or last-resort infusion schedule that can be used to maintain infusion of at least a minimum therapeutic amount of the therapeutic agent to patient 1 until a physician or other clinician is able to reprogram IMD 12.

Processor 34 controls the operation of medical pump 42 with the aid of software instructions associated with program information that is stored in memory 36. In one example, processor 34 is configured to run the software instructions in order to control operation of fluid delivery device 12. The software instructions may define therapy programs that specify the amount of a therapeutic agent that is delivered to a target tissue site within patient 1 from reservoir 32 via catheter 14, e.g., dose, the rate at which the agent is delivered, e.g., dosage rate, and the time at which the agent will be delivered and the time interval over which the agent will be delivered, e.g., the infusion schedule for dose or doses defined by program. In other examples, a quantity of the agent may be delivered according to one or more physiological characteristics of a patient, e.g., physiological characteristics sensed by one or more sensors (not shown) implanted within a patient as part of therapy system 10 (FIG. 1). Processor 34 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Processor-controlled memory 36 may include any volatile or non-volatile media, such as a random access memory (RAM), read only memory (ROM), non-volatile RAM (NVRAM), electrically erasable programmable ROM (EEPROM), flash memory, and the like. As mentioned above, memory 36 may store program information including instructions for execution by processor 34, such as, but not limited to, therapy programs, historical therapy programs, timing programs for delivery of the therapeutic agent from reservoir 32 to catheter 14, and any other information regarding therapy of patient 1. In one example, shown in FIG. 2, memory 36 includes a ROM portion 50, a RAM portion 52, and a flash memory portion 54. Memory 36 may include separate memory portions for storing instructions, patient information, therapy parameters (e.g., grouped into sets referred to as "dosing programs"), therapy adjustment information, program histories, and other categories of information such as any other data that may benefit from separate physical memory modules. For example, software instructions may be stored on ROM 50 and/or flash memory 54, while therapy parameters or adjustment information may be stored on RAM 52. Multiple copies of each of the foregoing types of information may be stored in different memory portions within memory 36 for redundancy or backup of the information.

Hardware controller 44 may directly control the hardware of medical pump 42. Hardware controller 44 receives instructions regarding the delivery of therapeutic agent from processor 34, such as an infusion rate corresponding to a therapy program stored in memory 36, and controls medical pump 42 accordingly. For example, if a therapy program 64 stored in memory 36, described in more detail below, dictates that at a particular point in time, IMD 12 should be delivering a particular dosage rate of the therapeutic agent to patient 1, processor 34 instructs hardware controller 44 to provide the particular dosage rate, and hardware controller 44 causes the actuating device of medical pump 42, such as rollers in a peristaltic pump or a piston in a piston pump, to be actuated at the rate that will provide the particular dosage rate. Hardware controller 44 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "controller" may generally refer to any of the foregoing logic circuitry, alone or in combination with other logic circuitry, or any other equivalent circuitry. Hardware controller 44 may also include a hardware-controlled memory 56 that stores parameters associated with control of medical pump 42, for example trim parameters such as voltage references and bias currents. Hardware-controlled memory 56 may include any volatile or non-volatile media, such as hardware registers random access memory (RAM), read only memory (ROM), non-volatile RAM (NVRAM), electrically erasable programmable ROM (EEPROM), flash memory, hardware registers and the like.

Telemetry module 38 in IMD 12, as well as telemetry modules in programmers, such as external programmer 20, provides communication between IMD 12 and external programmer 20. Communication with telemetry module 38 may be accomplished by any communication mechanism, such as local wireless communication techniques including, but not limited to, RF communication according to the 802.11 or Bluetooth specification sets, ZigBee communication standards, infrared (IR) communication according to the IRDA specification set, or other standard or proprietary telemetry protocols. In addition, telemetry module 38 may communicate with programmer 20 via proximal inductive interaction of IMD 12 with external programmer 20. Processor 34 controls telemetry module 38 to send from and receive information to IMD 12.

Power source 40 delivers operating power to various components of IMD 12. Power source 40 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

Alarm 49 alerts the patient of a condition within IMD 12, such as the detection of an error condition and/or the use of default infusion schedule 70 to deliver the therapeutic agent. Alarm 49 may be any device that may come to a patient or clinicians attention such as an audible alarm that is heard by the patient, a vibrational alarm that is felt by the patient, or a signal sent by IMD 12 to another device, such as an external computing device, for example programmer 20.

Figure 3:
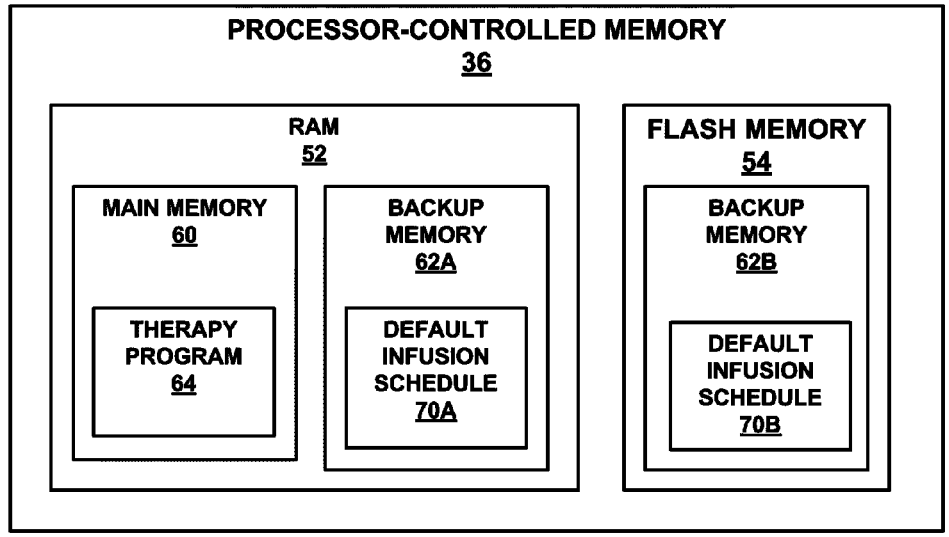
FIG. 3 is a functional block diagram illustrating an example processor-controlled memory that may be included in an implantable fluid delivery device.
Figure 4:
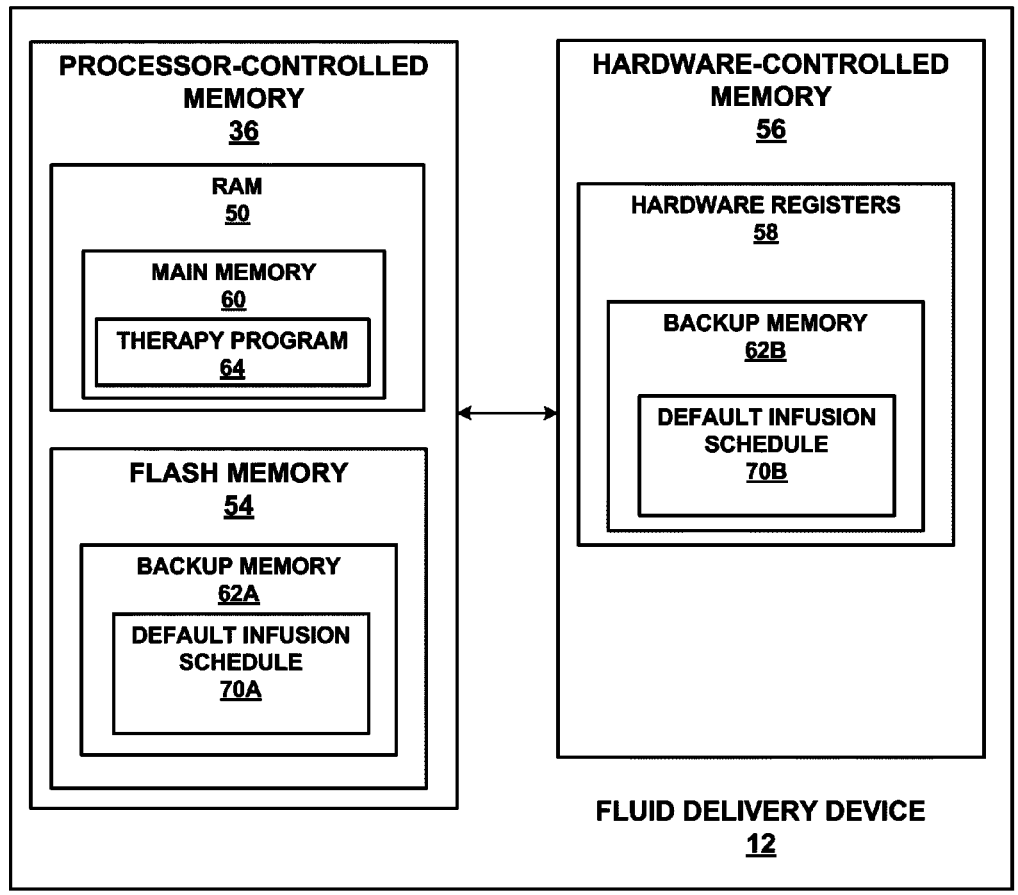
FIG. 4 is a functional block diagram illustrating example processor-controlled memory and hardware-controlled memory within an implantable fluid delivery device.

In general, IMD 12 includes memory including a main memory portion and a backup memory portion. The terms "main memory" and "backup memory" are not meant to be limiting, but rather are intended to provide clarity. In general, the main memory portion may include data, instructions, or parameters that may be considered to be used as part of the normal operation of IMD 12 while the backup memory portion may include data, instructions, and parameters that provide redundancy or backup of the normal operation of IMD 12. However, anything described as being stored in a portion of memory designated "main memory" herein can also be stored in a portion of memory referred to herein as "backup memory" and vice versa. In addition, data may be redundantly stored in both a portion labeled as "main memory" herein and in a portion labeled "backup memory." In the example of FIG. 2, processor-controlled memory 36 includes main memory 60 and backup memory 62. However, as illustrated in FIGS. 3 and 4, in other examples, the main memory and backup memory included in the memory of IMD 12 may be allocated to different specific memory components, e.g., split between processor-controlled memory 36 and hardware-controlled memory 56. Additionally, in the example shown in FIG. 2, main memory 60 is a portion of RAM 52 of processor-controlled memory 36, however, different types of memory of the processor-controlled memory 36, e.g., ROM 50 or flash memory 54, may also be used as main memory 60. As with main memory 60, although backup memory 62 is a portion of flash memory 54 of processor-controlled memory 36 in the example of FIG. 2, different types of memory, e.g., a portion of RAM 52 or ROM 50 of the processor-controlled memory 36 or hardware registers 58 or another component of hardware-controlled memory 56 may be used as backup memory 62.

The main memory and backup memory may be part of the same type of memory, such as main memory 60 and backup memory 62A both being a part of RAM 52 as in the example of FIG. 3. In such an example, the main memory and the backup memory may each be part of a separate memory, e.g., a separate memory chip or different sections of the same memory chip, or the main memory and the backup memory may merely be separate portions of the same memory.

In FIG. 2, therapy program 64 corresponding to the delivery of a therapeutic agent to patient 1 is stored in main memory 60. The therapy program may also be stored in backup memory 62, such as to provide storage redundancy. Default infusion schedule 70 is stored in backup memory 62. The default infusion schedule may also be stored in main memory 60 as well as backup memory 62, such as to provide storage redundancy. Default infusion schedule 70 is based on therapy program 64 for patient 1 such that default infusion schedule 70 is specific to patient 1, IMD 12, and/or the therapeutic agent being delivered by the device to the patient. An identifier (not shown) may be stored in order to identify default infusion schedule 70 to a particular time or infusion schedule. For example, if therapy program 64 includes a schedule with different infusion patterns each day, such as infusion schedule 74 described below with respect to FIG. 6, then at the beginning of each day, processor 34 may store the identifier to indicate which day it is, so that if an error condition is detected, processor will be able to know on which day of a corresponding default infusion schedule 70 to start. For example, on Day 1 of therapy program 74, which may be a Monday, processor 34 may store an identifier indicating that it is Day 1. If no error condition occurs during Day 1, then at the start of Day 2, processor 34 may store a new identifier, replacing the previous identifier that indicates it is Day 2. However, if an error condition does occur during Day 1, then when IMD 12 reverts to default infusion schedule 70, it will start infusion at the beginning of Day 1 of default infusion schedule 70. Periods of time other than full days may be used with the identifier, such as hourly, every eight hours, every 12 hours, every 16 hours, every 20 hours, and so on. In one example, the identifier is stored in backup memory 62 along with default infusion schedule 70.

An error-detection check, such as a cyclic redundancy check (CRC), may also be provided in order to check for data corruption or other errors within therapy program 64 and default infusion schedule 70. In one example, a first CRC is stored in main memory 60 to check for data corruption or other errors within therapy program 64 while a second CRC is stored in backup memory 62 to check for data corruption or other errors within default infusion schedule 70. In one example, a CRC is stored along with the data that it will check for data corruption or other errors, such as storing the first CRC in the same location within main memory 60 as therapy program 64 and storing the second CRC in the same location within backup memory 62 as default infusion schedule 70. Processor 34 of IMD 12 is configured to determine an error condition within IMD 12 that prevents the continued use of therapy program 64 without unnecessary risk to patient 1, and upon determining the existence of such an error condition, to cease using therapy program 64 and to instead use default infusion schedule 70 for delivery of the therapeutic agent to patient 1.

An error condition that prevents the reliably use of therapy program 64 may be any error that either causes the stored therapy program to be unreliable or that renders IMD 12 unable to reliably implement the stored therapy program. An example of such an error condition is therapy program 64 being corrupted in main memory 60. If therapy program 64 is redundantly stored in other memories, such as backup memory 62, than an error condition would not exist unless there is corruption in the redundantly stored copies as well.

Another example of an error condition is IMD 12 losing its time point when therapy program 64 includes a time-varying infusion schedule. A loss of time point may comprise a total loss of time point, wherein IMD 12 is unable to determine the present time and is unable to reliably measure the passage of time after the loss of the present time point, or a partial loss of time point, wherein IMD 12 does not know the present time, but can reliably keep track of time going forward. A total loss of time point may occur, for example, if the device that is used to measure time within IMD 12, such as an oscillator circuit, for example a crystal oscillator, becomes corrupt or unreliable such that IMD 12 cannot reliably measure the passage of time. A partial loss of time may involve an error wherein the present time is lost for some reason, but wherein the time-measuring device is still reliable.

In one example, IMD 12 may include two or more independent time-measuring devices, also referred to as a time reference or time origin, that may be cross-checked to provide redundancy of time keeping. For example, IMD 12 may comprise two separate time-keeping devices that run independent from one another, such as two separate oscillator circuits, for example two separate crystal oscillators or two separate electrical oscillator circuits or processors. A first time-keeping device is used by processor 34 as the primary device to direct infusion of the therapeutic agent according to an infusion schedule of therapy program 64. After certain time frequencies, processor 34 may compare the time values of the first time-keeping device and the second time-keeping device and determine if they are still in sync, within a predetermined threshold. In one example, processor 34 may compare the time values from each time-keeping device between about every on-thousandth of a second and about every day, such as every second, every minute, every fifteen minutes, every thirty minutes, every hour, every two hours, every four hours, every twelve hours, etc. If processor 34 discovers that the two time-keeping devices are in sync, then processor 34 can be confident that there is no loss in time point. If the time-keeping devices are out of sync, processor 34 may update an errant time-keeping device with the correct time point. In one example, processor 34 analyzes each time-keeping device to determine if there is an error with one of them that explains the out-of-sync finding. If processor 34 determines that only one time-measuring device is in error, and can determine which time-measuring device has the error, it reinitializes the errant time-measuring device to the correct time point using the other, non-errant, device. If processor 34 either determines that both time-measuring devices are in error or cannot determine which time-measuring device is in error, then processor 34 determines that there is a loss of time point that requires reversion to default infusion schedule 70. In one example, whenever processor 34 checks if the time-keeping devices are synchronized, processor 34 sets a synchronization marker so that if processor 34 has any reason to doubt the reliability of the time point provided by the primary time-keeping device, then processor 34 will determine the amount of time that has elapsed since the last synchronization check as measured by the second time-keeping device to determine what point in time processor 34 may resume using an infusion schedule of therapy program 64. Additional time-measuring devices, such as additional oscillator circuits, for example oscillator crystals or electrical oscillator circuits or processors, may be used beyond just two such devices. For example, IMD 12 may include three, four, five, or more time-measuring devices.

Another example error condition includes therapy program 63 failing a runtime check, such as a parameter within therapy program 64 being out of bounds or a parameter pointing to an invalid or unused spaced within therapy program 64 that may be due to a programmer error when encoding therapy program 64. Other example error conditions include software errors, e.g., errant pointers, memory corruption, or stack overflow, that cause reinitializing of IMD 12, at which point IMD 12 is unable to deliver a time-varying infusion schedule. In one example, any error or corruption within IMD 12 that may be interpreted as corresponding to a loss or corruption of time point may be considered an error condition that warrants the use of default infusion schedule 70. Examples of such errors or corruptions include detection of a stack overflow, an errant pointer that may have caused random writes to memory or random memory corruption if the random writing or corruption is believed to have included a memory area that maintains time point, program code going down an unexpected path (e.g., into a default statement of a switch type construct where based on normal execution, the code should not go through a default case, or in a else clause where one is not valid), an exception thrown by code, memory allocation or deallocation errors, and general memory management issues.

Another example error condition may occur when, following an unexpected pump reset, IMD 12 is unable to deliver the therapy program, in particular a time-varying infusion program. During operation of IMD 12, an error or corruption may occur that requires the reset of the hardware of IMD 12. If the error or corruption is detected by IMD 12, such as by processor 34, then the reset may be a "planned" reset, wherein processor 34 stores a log of the error or corruption so that after the reset, processor 34 may read the log and know exactly what caused the reset. However, in some cases, IMD 12 may reset for an unknown reason such that no log of the error was made. In such a case, processor 34 may not know and may be unable to determine what caused the unexpected reset, and in order to ensure patient safety, processor 34 may assume that the error that caused the unexpected reset is one wherein implementation of the stored therapy program would be unreliable, such that processor 34 determines that the default infusion schedule 70 should be used instead. Examples of pump resets that may be considered error conditions for purposes of the present disclosure include (a) a pump reset wherein the error or problem that caused the reset is known or discoverable by processor 34, but wherein the error or problem cannot be corrected without reprogramming IMD 12; and (b) a pump reset wherein the error or problem that caused the reset is unknown, e.g., an unexpected reset, wherein it is assumed that the error or problem is serious enough that delivery according to therapy program 64 may be unreliable because of the unknown nature of the error.

Other example error conditions occur when pump hardware, such as hardware controller 44, determines that processor 34 or the pump software is not functioning correctly. One example of this type of error condition is a failure in the timing or another defined parameter of the communication between processor and hardware controller 44, e.g., an improper handshake between processor 34 and hardware controller 44. Another example of an error condition of a malfunctioning processor 34 or pump software is a failure of a crosschecking between hardware and software of fluid delivery device 12, such as an incorrect strobing of a watchdog timer associated with hardware controller 44, wherein processor 34 fails to communicate with the watchdog timer at a predetermined, repeating time interval, e.g., processor 34 fails to "strobe" the watchdog timer. Mechanisms other than handshaking or a watchdog timer may be used to crosscheck between hardware controller 44 and processor 34.

Another example error condition is a detection, e.g., by processor 34, of a possible malicious attempt by an external programmer that could harm patient 1. Processor 34 may be configured to determine that an external programmer that is attempting to modify the therapy program on fluid delivery device 12 is an unauthorized external programmer. Processor 34 may also be configured to determine that changes made to the therapy program, even if by an authorized external programmer, are malicious such that processor 34 determines it should revert to a safe, default infusion schedule, e.g., stored in the backup memory 62.

Another error condition is the determination by processor 34 that parameters provided by therapy program 64 stored in memory 36 are incorrect, inconsistent, or invalid. Examples of incorrect parameters include a provided parameter being outside of general boundaries specified by therapy program 64 or IMD 12 or that the provided parameter conflicts with another parameter provided by therapy program 64. For example, therapy program 64 may specify boundaries such that a particular parameter may only have values between 0 and 200, but may also provide a specific instruction that, when encoded in an 8-bit number, comes to a value of 216. In another example, therapy program 64 may indicate that it includes a weekly infusion schedule (bounded as a seven day schedule) that includes eight days. In such a case, the conflict between the boundaries and the specific instruction may be determined to be an error condition that results in processor 34 determining that default infusion schedule 70 should be used. Examples of inconsistent parameters include those resulting in conflicting information, such as two parameters that cannot coexist, or conflicting instructions, such as two instructions that cannot both be executed. Examples of invalid parameters, or an invalid therapy program 64, include encoding of a therapy program 64 that shows it should be run, but the therapy program 64 has not been initialized or it has been invalidated.

Yet another error condition may be a pump stoppage having a duration longer than a predetermined time. For example, fluid delivery device 12 may be instructed by a clinician through external programmer 20 to stop the therapy program to perform a procedure, such as refilling reservoir 32 or a testing procedure of patient 1, such as a magnetic resonance imaging (MRI) scan. Typically, fluid delivery device 12 is restarted after the procedure is complete. The clinician may forget to restart fluid delivery device 12, however, and both patient 1 and the clinician may be unaware that fluid delivery device 12 is no longer infusing the therapeutic agent. In another example, patient 1 may be taken off the therapy provided by fluid delivery device 12 for an extended period of time, such as for a week or a month while patient 1 is being treated for an infection that may be compromised by continued infusion of the therapeutic agent delivered by fluid delivery device 12. Processor 34 or hardware controller 44 may be configured so that when an instruction to stop for a procedure or for an extended discontinuation of therapy is initiated, an error condition is triggered when fluid delivery device is not restarted after a predetermined period of time that is sufficient for the procedure or discontinuation of therapy to be completed, e.g., an hour or two hours after the instruction to stop for an MRI scan is provided from external programmer 20 or after a discontinuation of therapy continues for more than 24 hours beyond the time period planned. Once the predetermined period of time has elapsed, fluid delivery device 12 will treat it as an error condition that necessitates use of a default infusion schedule 70 to resume direct delivery of the therapeutic agent.

The processor that is configured to determine the existence of an error condition may be one or more of any processor, microprocessor, digital signal processor (DSP), application specific integrated circuit (ASIC), field programmable gate array (FPGA), programmable logic circuit, or the like, either alone or in any suitable combination, within IMD 12. In the example shown in FIG. 2, the processor can be processor 34 or hardware controller 44. For example, processor 34 may be configured to determine the existence of any or all of the error conditions described above, such as a corruption of the therapy program 64 in memory 36 or a loss of time point.

In another example, hardware controller 44 may be configured to determine that processor 34 or software within IMD 12 is not functioning properly, such as an incorrect timing of communication between processor 34 and hardware controller 44 or incorrect strobing of a watchdog. In another example, both processor 34 and hardware controller 44 may be configured to determine the existence of error conditions. For example, processor 34 may be configured to detect error conditions in which processor 34 is still functional, such as a corruption of the therapy program in memory 36 or a loss of time point, while hardware controller 44 may be configured to detect error conditions in which processor 34 or IMD software are malfunctioning. In yet another example, processor 34 is configured to detect an error condition within IMD 12 and, upon detection, to instruct hardware controller 44 to use default infusion schedule 70. Hardware controller 44 is then responsible for changing IMD 12 from the infusion schedule of therapy program 64 to default infusion schedule 70.

Figure 5:
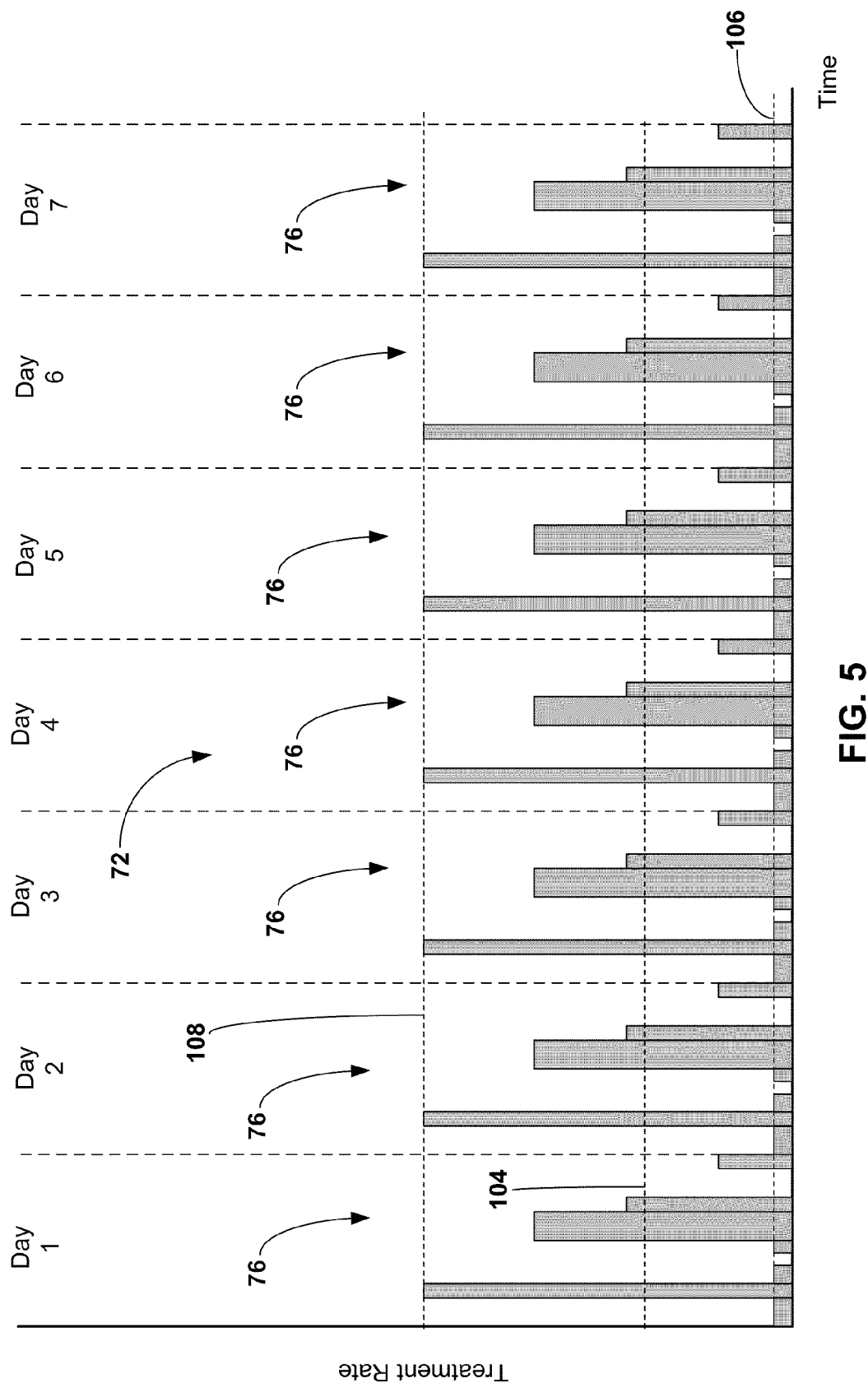
FIG. 5 is a diagram illustrating an example infusion schedule of a therapy program for the patient wherein an infusion pattern is repeated daily.
Figure 6:
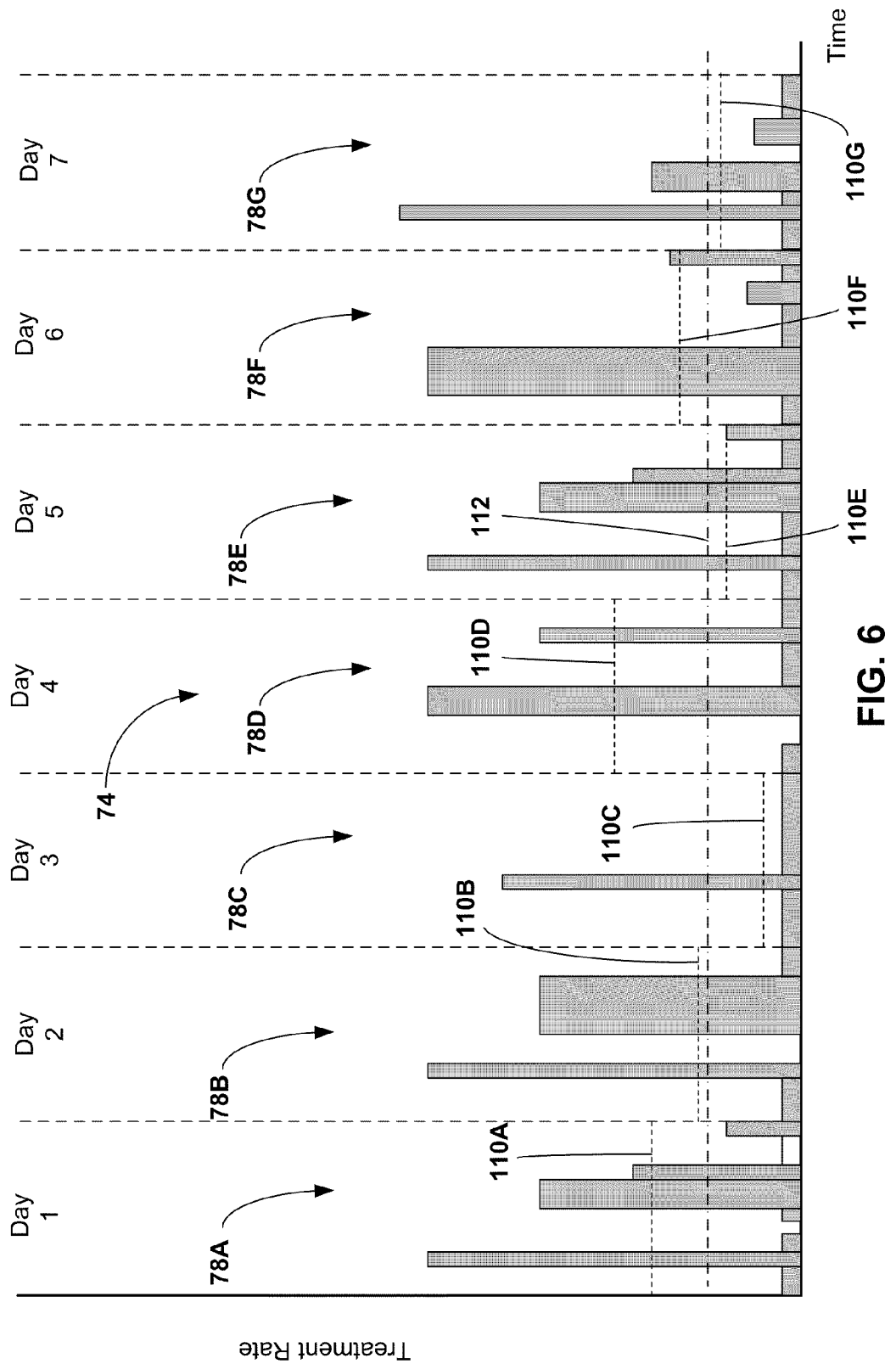
FIG. 6 is a diagram illustrating another example infusion schedule of a therapy program for the patient wherein each day comprises a different infusion pattern.

Therapy program 64 corresponds to the delivery of a specific therapeutic agent to a specific patient 1 and may include therapy parameters, as described above, including therapeutic agent doses and dose rates. Therapy program 64 includes an infusion schedule to be used during therapy of patient 1, such as the example infusion schedules 72, 74 shown in FIGS. 5 and 6. As shown in FIGS. 5 and 6, infusion schedules 72, 74 may be time-varying such that the dosage rate that is delivered to patient 1 varies over time, as determined and prescribed, e.g., by a clinician treating patient 1. In the example of FIG. 5, infusion schedule 72 is a time-varying schedule, sometimes referred to as a "flex" schedule, which includes a common infusion pattern 76 that is repeated daily, such that the infusion pattern 76 on Day 1 is the same as the infusion pattern for Days 2, 3, 4, and so forth.

In the example of FIG. 6, infusion schedule 74 is a flex schedule including a number of infusion patterns applied over the course of a number of days. In particular, infusion schedule 74 includes a first infusion pattern 78A on Day 1, a second infusion pattern 78B on Day 2, a third infusion pattern 78C on Day 3 (collectively referred to as "infusion pattern 78"), and so forth. Although FIG. 6 shows each day having a different infusion pattern 78, infusion schedule 74 could include repeated patterns, such as a first infusion pattern on Days 1, 3, and 5, a second infusion pattern on Days 2 and 4, and a third infusion pattern on Day 7 (not shown).

Therapy program 64 stored on main memory 60 of processor-controlled memory 36 in the example of FIG. 2 may also include other parameters that may be used to determine default infusion schedule 70 stored on backup memory 62, such as parameters specific to a particular therapeutic agent. For example, therapy program 64 may include parameters regarding whether the therapeutic agent delivered to patient 1 by IMD 12 has higher risks associated with over infusion or under infusion and the condition being treated by the therapeutic agent. Additionally, therapy program 64 may include parameters specific to patient 1, including, e.g., patient weight, body composition, the infusion history of patient 1, including dosage history and/or side-effects associated with that dosage history.

The infusion history may be for the current therapeutic agent being delivered by IMD 12 to patient 1 or for similar and related therapeutic agents that were previously delivered to patient 1. In the example shown in FIG. 7, therapy program 64 includes the delivery history 80 of the therapeutic agent to patient 1. In this example, patient 1 was prescribed the same infusion schedule 74 that is shown in FIG. 6, but was permitted to set patient-initiated rate changes 82A, 82B and to infuse a patient-initiated bolus 84. Because delivery history 80 is different than the prescribed infusion schedule 74, default infusion schedule 70 may be determined based on delivery history 80 rather than infusion schedule 74, or default infusion schedule 70 may be determined based on some combination of the prescribed infusion schedule 74 and the actual delivery history 80, such as an average of the two.

Generally speaking, default infusion schedules employed in the disclosed examples provide a backup or last-resort infusion schedule that can be used to maintain infusion of at least a minimum therapeutic amount of the therapeutic agent to patient 1 until a physician or other clinician is able to reprogram IMD 12. A "therapeutic amount" generally refers to an amount of the therapeutic agent that has some minimally-acceptable therapeutic effect in treating the condition for which patient 1 is receiving the therapeutic agent infusion. In one example, a "therapeutic amount" is the minimum amount that is necessary to prevent withdrawal by patient 1 due to under infusion of the therapeutic agent.

In another example, a "therapeutic amount" is the minimum amount that is necessary to achieve a desired therapeutic result in patient 1, such as to achieve pain management for the patient 1 that, even if pain or discomfort is not eliminated, is tolerable by the patient, or to sufficiently dampen spasticity such that the patient is able to function, even if the spasticity is not completely eliminated. In this way, in the event of an error condition affecting therapy program 64, default infusion schedule 70 allows IMD 12 to continue at least a minimally-effective delivery of the therapeutic agent to patient 1 rather than shutting IMD 12 down or resorting to a non-patient and non-therapeutic agent specific base rate installed in IMD 12 at fabrication.

Default infusion schedule 70 may be determined based on therapy program 64, for example, by being calculated based on a prescribed therapy infusion schedule, such as infusion schedule 72 or 74 of FIGS. 5 and 6, respectively, patient delivery history 80 of FIG. 7, or some other factor, as described in more detail below. In one example, default infusion schedule 70 is a simplified or less sophisticated version of infusion schedule 72 or 74 so that the time-varying dependency of therapeutic agent delivery is minimized or eliminated when the therapeutic agent is delivered according to the default infusion schedule. For example, the default infusion schedule may be a constant fixed default infusion rate that is calculated based on the dosage rate or rates of therapy program 64. However, in other examples, the default infusion schedule can be other simplified forms of therapy program 64, such as a particular fixed rate or rate schedule for certain time periods that correspond to the therapy program, for example separate fixed rates for each day of the week or for specific times of day (e.g., morning, afternoon, evening, and night).

In another example, more than one default infusion schedule can be provided to vary depending on the type of error condition encountered by IMD 12. In one example, default infusion schedule 70 may comprise a plurality of default infusion schedules that are created and stored in IMD 12 in order to respond to a variety of error conditions. For example, default infusion schedule 70 may comprise a first default infusion schedule that is a fixed default infusion rate that IMD 12 can resort to in the event that the error condition involves a total loss of the time point such that IMD 12 processor 34 has completely lost its ability to determine the present time and the ability to determine where IMD 12 is in infusion schedule 72 or 74.

A second default infusion schedule may provide an intermediate response for a situation where processor 34 has lost the present time, but knows where IMD 12 was in therapy program 64 at the time the error condition arose, such that processor 34 has, in essence, a general knowledge of where it is in infusion schedule 72 or 74. In such a case, the second default infusion schedule may provide for daily average dosage rates starting from the point the error condition occurred, such as daily average rates 110A for Day 1, 110B for Day 2, 110C for Day 3, and so on (FIG. 6). Finally, a third default infusion schedule may be a direct copy of infusion schedule 72 or 74 of therapy program 64, for the case where the error condition is solely a corruption of therapy program 64 in memory 36, but wherein processor 34 has not lost the time point or the position of IMD 12 within therapy program 64. The third default infusion schedule can be used to write over the corrupted infusion schedule 72, 74 so that IMD 12 can continue with the prescribed infusion schedule. In this way, IMD 12 can take the most sophisticated response to the error condition.

Default infusion schedule 70 may be determined by any processor, or similar device, capable of calculating default infusion schedule 70 based on therapy program 64 and any other information in the manner described above. In one example, processor 26 in external programmer 20 determines default infusion schedule 70. In this example, therapy program 64 may be stored on memory of external programmer 20 and employed by processor 26 to determine default infusion schedule 70. Once default infusion schedule 70 is determined, the default infusion schedule and therapy program 64 may be transmitted to IMD 12 by programmer 20 and stored in memory, e.g., backup memory 62 and main memory 60, respectively. In another example, at least one of processor 34 or hardware controller 44 of IMD 12 may determine default infusion schedule 70 based on therapy program 64 (and any other relevant information) stored on main memory 60 or, in some examples prior to the completion of programming IMD 12, a memory of external programmer 20.

In another example, rather than storing different default infusion schedules to respond to different error conditions, IMD 12 may be configured so that the default infusion schedule 70 is determined upon detection of the error condition, such that the type of default infusion schedule that is used can be appropriate for the type of error condition. For example, if the error condition involves a complete loss of time point wherein IMD 12 does not know the present time and is also unable to accurately measure the passage of time going forward, then processor 34 may calculate a fixed default infusion rate to act as default infusion schedule 70 until IMD 12 can be reprogrammed. If, however, the error condition only involves a partial time loss whereby IMD 12 knows the day when the error condition occurred, but not the time of the day, and IMD 12 is able to reliably measure time going forward, then processor 34 may determine a default infusion schedule, which may be a fixed rate, for the next 24 hours. After the passage of this initial 24 hours, processor 34 may again calculate a new default infusion schedule for the following 24 hours. This process can be repeated for each cycle of 24 hours until IMD 12 is reprogrammed. Time durations other than 24 hours may be used, such as an hourly time cycle, a four-hour time cycle, a six-hour time cycle, a twelve-hour time cycle, and so on.

As described above with respect to FIG. 2, in one example, default infusion schedule 70 is stored in backup memory 62 of processor-controlled memory 36 while therapy program 64 is stored in main memory 60. Main memory 60 and backup memory 62 can be any memory within IMD 12, such as a processor-controlled memory 36, including ROM 50, RAM 52, or flash memory 54, or a hardware-controlled memory 56 such as hardware registers 58 associated with hardware controller 44. In one example, main memory 60 is a portion of a processor-controlled memory 36, such as a portion of RAM 52 as shown in FIG. 2, and backup memory 62 is a different portion of processor-controlled memory 36, such as a portion of flash memory 54 as shown in FIG. 2. Backup memory 62 containing default infusion schedule 70 may be a portion of the same type of memory as main memory 60 containing therapy program 64. In the example of FIG. 3, main memory 60 and backup memory 62A are both part of RAM 52. Alternatively, backup memory 62 may be a portion of a different type of memory as main memory 60. In on example shown in FIG. 3, the backup memory 62B is a portion of flash memory 54 of processor-controlled memory 36, while main memory 60 is a portion of RAM 52. In another example shown in FIG. 4, backup memory 62B is a part of hardware registers 58 of hardware-controlled memory 56, while main memory 60 is a portion of RAM 50 of processor-controlled memory 36.

Default infusion schedule 70 may also be redundantly stored in more than one backup memory 62 by storing a first copy of default infusion schedule 70A in one portion of memory and redundantly storing a second copy of default infusion schedule 70B in the same type of memory or a different type of memory as the first copy. In one example, shown in FIG. 3, a first copy of default infusion schedule 70A is stored in a first backup memory 62A that is a first portion of processor-controlled memory 36, e.g., a portion of RAM 52, while a second redundant copy of default infusion schedule 70B is stored in a second backup memory 62B that is another portion of processor-controlled memory 36, e.g., a portion of flash memory 54, or another portion of RAM 52 (not shown). In another example, shown in FIG. 4, a first copy of default infusion schedule 70A is stored in a first backup memory 62A that is a portion of processor-controlled memory 36, e.g., a portion of flash memory 54, while a second copy of default infusion schedule 70B is stored in a second backup memory 62B that is a portion of a hardware-controlled memory 56, e.g., a portion of hardware registers 58.

Redundant storage of default infusion schedule 70 provides an additional backup in the event the first copy of default infusion schedule 70A is found, e.g., by processor 34, to be corrupted or not valid for some other reason, in which case the processor may use the second copy 70B to update the first copy 70A and/or use the second copy 70B as the operating infusion schedule. In another redundant storage example, default infusion schedule 70 is stored in such a way that a copy of default infusion schedule 70 is accessible to each of processor 34 and hardware controller 44. This example may be useful to allow IMD 12 to respond to error conditions in which processor 34 is functioning properly but therapy program 64 should not be used, and to respond to error conditions in which processor 34 or the IMD software is not functioning properly. In this example, default infusion schedule 70 may be stored in a backup memory 62 that is accessible to both processor 34 and hardware controller 44, or default infusion schedule 70 may be stored in a first backup memory 62A that is a portion of a processor-controlled memory 36, such as flash memory 54 shown in FIG. 4, for access by processor 34, and in second backup memory 62B that is a portion of a hardware-controlled memory 56, such as in hardware registers 58 as shown in FIG. 4, for access by hardware controller 44.

Figure 8:
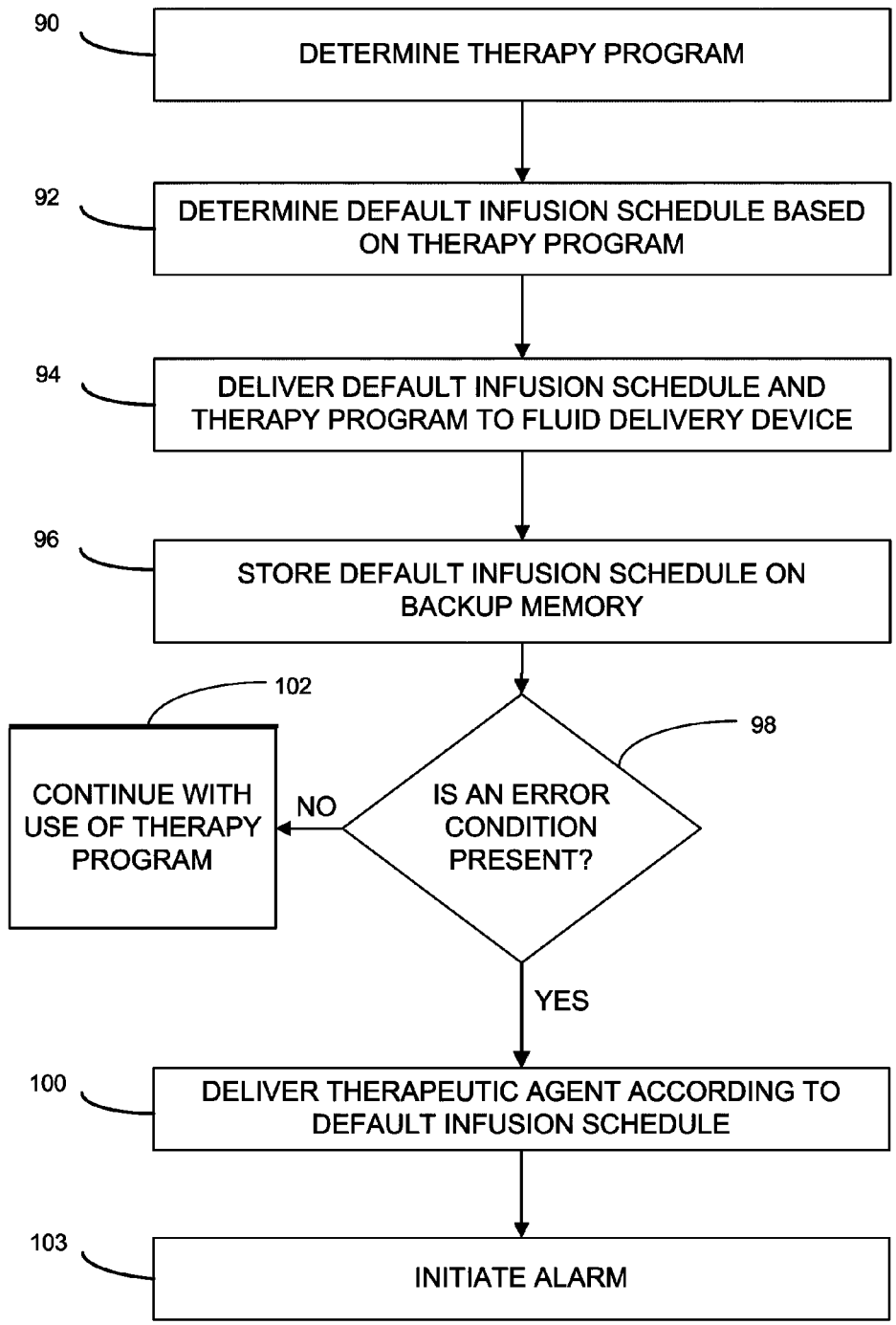
FIG. 8 is a flowchart showing a method of storing and using a default infusion schedule based on a therapy program of the patient.

FIGS. 8 and 10-13 are flow charts illustrating several example methods related to the determination and use of default infusion schedules. FIG. 8 is directed to a general example of determining a default infusion schedule based on a prescribed therapy program and using the default infusion schedule in the event an error condition is detected. FIGS. 10-13 are directed to several example methods of storing one or more default infusion schedules, e.g., on memory of an IMD, and of detecting various error conditions that necessitate use of the default infusion schedules. For illustrative purposes, the various functions included in the example methods illustrated in FIGS. 8 and 10-13 are described below as executed by one of processor 34 or hardware controller 44 of IMD 12, or processor 26 of programmer 20. However, these functions may all be executed by a single processor, or different combinations of these functions may be executed by different combinations of processor 34 and hardware controller 44 of IMD 12, and processor 26 of programmer 20, as well as processors of other external devices.

The example method of FIG. 8 includes determining therapy program 64 (90); determining a default infusion schedule based on a therapy program 64 specific to patient 1 (92); delivering default infusion schedule 70 and therapy program 64 to IMD 12 (94); storing default infusion schedule 70 on a backup memory 62 of IMD 12 (96); determining if an error condition is present in IMD 12 such that IMD 12 cannot reliably deliver a therapeutic agent based on the therapy program 64 (98); if the error condition is present, delivering the therapeutic agent according to the default infusion schedule (100); and if the error condition is not present, continuing with the prescribed therapy program 64 (102). The method of FIG. 8 may also include initiating an alarm (103) indicating that the error condition was detected and that default infusion schedule 70 is being used.

In one example, determining the therapy program (90) and determining the default infusion schedule (92) may be performed by a processor of an external device, e.g., processor 26 of external programmer 20. In such examples, therapy program 64 and/or default infusion schedule 70 are delivered to IMD 12 (94), e.g., wirelessly via telemetry module 38. As explained above, default infusion schedule may be stored on backup memory 62 of IMD 12 (96). Additionally, therapy program 64 may be stored in main memory 60 of IMD 12. In examples in which determining therapy program 64 (90) is performed by external programmer 20, or another external device, the determination may be performed either by direct programming by a clinician or by an algorithm or program that automatically determines therapy program 64 based on parameters associated with the therapeutic agent, e.g., whether the therapeutic agent has higher risks associated with over infusion or under infusion and the condition being treated by the therapeutic agent, or parameters specific to patient 1, e.g., patient weight, body composition, and the infusion history of patient 1. In one example, a clinician enters therapy parameters to define therapy program 64 including, e.g., one or more therapeutic agent doses, dose rates, and a therapy infusion schedule for delivering the doses at particular times.

In another example, determining default infusion schedule 70 (92) may be performed by processor 34 or hardware controller 44 onboard IMD 12 based on therapy program 64 stored within main memory 60 of IMD 12. For example, as described in more detail below, processor 34 or hardware controller 44 may perform calculations or run an algorithm necessary to determine default infusion schedule 70. Additionally, in one example, processor 34 or hardware controller 44 may periodically verify that default infusion schedule 70 stored on backup memory 62 is uncorrupted and valid. If default infusion schedule 70 is found to be corrupted or invalid for some other reason, processor 34 or hardware controller 44 may re-determine the default infusion schedule based on therapy program 64 and replace the corrupted or invalid default infusion schedule with the re-determined default infusion schedule.

Determining default infusion schedule 70 based on therapy program 64 (92) can be accomplished according to a variety of specific methods. In one example, default infusion schedule 70 is determined using an algorithm that performs calculations based on therapy program 64 and that is executed by one or more of processor 26 of external programmer 20 or processor 34 or hardware controller 44 within IMD 12. The specific method employed to determine default infusion schedule 70 (92) may depend on the characteristics of therapy program 64. For example, if therapy program 64 comprises an infusion schedule that includes one fixed infusion rate, then determining default infusion schedule 70 (92) may only include copying the fixed therapy infusion rate as a fixed default infusion rate for default infusion schedule 70. However, if therapy program 64 includes a time-varying infusion schedule, such as infusion schedules 72 and 74 of FIGS. 5 and 6, respectively, then several methods of determining default infusion schedule 70 may be used.

In one example in which therapy program 64 includes a repeating daily "flex" infusion pattern, such as infusion pattern 76 of the example shown in FIG. 5, the default infusion schedule determination algorithm may be configured to determine the total daily dose for flex infusion pattern 76 and convert the total daily does to a fixed default infusion rate that achieves the total daily dose over a twenty-four hour period. In other words, the algorithm determines the average daily dosage rate, represented by line 104 in FIG. 5, and sets default infusion schedule 70 as a fixed default infusion rate that is equal to the average daily dosage rate 104. For example, in infusion schedule 72 shown in FIG. 5, each day comprises the same infusion pattern 76, which may result in a total infusion of 550 micrograms (mcg) of a therapeutic agent, or about 22.9 mcg of the therapeutic agent per hour, as represented by line 104 in FIG. 5. In this example, the default infusion schedule determination algorithm may determine that default infusion schedule 70 is to be a fixed default infusion rate of 22.9 mcg/hour, representing the average infusion rate for infusion schedule 72. In another example, default infusion schedule 70 may be set as a fixed default infusion rate that is equal to the minimum infusion rate that is delivered in accordance with infusion schedule 72, represented by line 106 in FIG. 5, or that is equal to a maximum infusion rate that is delivered in accordance with infusion schedule 72, represented by line 108 in FIG. 5.

In another example, therapy program 64 includes an infusion schedule with a number of different infusion patterns for different time periods, such as the example infusion schedule 74 shown in FIG. 6, which includes first infusion pattern 78A for Day 1, second infusion pattern 78B for Day 2, third infusion pattern 78C for Day 3, fourth infusion pattern 78D for Day 4, and so forth (collectively referred to as "infusion patterns 78"). In such an example, determining default infusion schedule 70 (90) may include configuring an algorithm to determine default infusion schedule 70 based on any number of calculations based on one or more of the different infusion patterns 78. For example, each day's infusion pattern 78 may correspond to a daily average infusion rate, such as average infusion rate 110A for Day 1 infusion pattern 78A, average infusion rate 110B for Day 2 infusion pattern 78B, and so on (collectively referred to herein as "daily average infusion rate(s) 110").

Default infusion schedule 70 may be set as a fixed default infusion rate based on one of the average infusion rates 110, such as the minimum daily average infusion rate 110, which, in the example of FIG. 6 is daily average infusion rate 110C for Day 3 infusion pattern 78C. Additionally, default infusion schedule 70 may be set as the most common (or modal) daily average infusion rate 110, wherein daily average infusion rates may be rounded to a particular number of significant figures so that rates that are close to one another can be considered to be equal for purposes of the modal determination. In another example, default infusion schedule 70 may be set as the maximum average infusion rate 110, e.g., daily average infusion rate 110D for Day 4 infusion pattern 78D in FIG. 6, a median daily average infusion rate 110, e.g., daily average infusion rate 110B for Day 2 infusion pattern 78B, or the average of the entire infusion schedule 74, represented by line 112 in FIG. 6.

Referring to one particular example of infusion schedule 74 of FIG. 6, Day 1 infusion pattern 78A may total 550 mcg for all of Day 1, corresponding to a daily average infusion rate 110A of about 22.9 mcg/hour. Day 2 infusion pattern 78B may total 425 mcg, corresponding to a daily average infusion rate 110B of about 17.7 mcg/hour. Day 3 infusion pattern 78C may total 100 mcg, corresponding to a daily average infusion rate 110C of about 4.2 mcg/hour. Day 4 infusion pattern 78D may total 650 mcg, corresponding to a daily average infusion rate 110D of about 27.1 mcg/hour. Day 5 infusion pattern 78E may total 300 mcg, corresponding to a daily average infusion rate 110E of 12.5 mcg/hour. Day 6 infusion pattern 78F may total 450 mcg, corresponding to a daily average infusion rate 110F of about 18.8 mcg/hour. Day 7 infusion pattern 78G may total 325 mcg, corresponding to a daily average infusion rate 110C of about 13.5 mcg/hour. These example values for infusion patterns 78 and daily average infusion rates 110 correspond to a total infusion of the therapeutic agent of 2,800 mcg over the entire infusion schedule 74, which averages out to about 16.7 mcg per hour over the entire seven-day (168 hour) period of infusion schedule 74.

Assuming the foregoing values for infusion schedule 74, a default infusion schedule determination algorithm may set default infusion schedule 70 as a fixed default infusion rate equal to the minimum daily average infusion rate 110, e.g., the 4.2 mcg/hour rate 110C from Day 3. The default infusion schedule determination algorithm may also set default infusion schedule 70 as a fixed default infusion rate equal to the median daily average infusion rate 110, e.g., the 17.7 mcg/hour rate 110B from Day 2. Default infusion schedule 70 may also be set as a fixed default infusion rate equal to the average of the daily average infusion rates 110, e.g., 16.7 mcg per hour, represented by line 112 in FIG. 6, or the maximum daily average infusion rate 110, e.g., the 27.1 mcg/hour rate 110D from Day 4. Although the example method described in relation to FIGS. 5 and 6 describe determining default infusion schedule 70 based on daily infusion patterns 76 and 78, respectively, the infusion patterns of other time periods can be used, such as hourly, every twelve hours, daily, or weekly.

Figure 9:
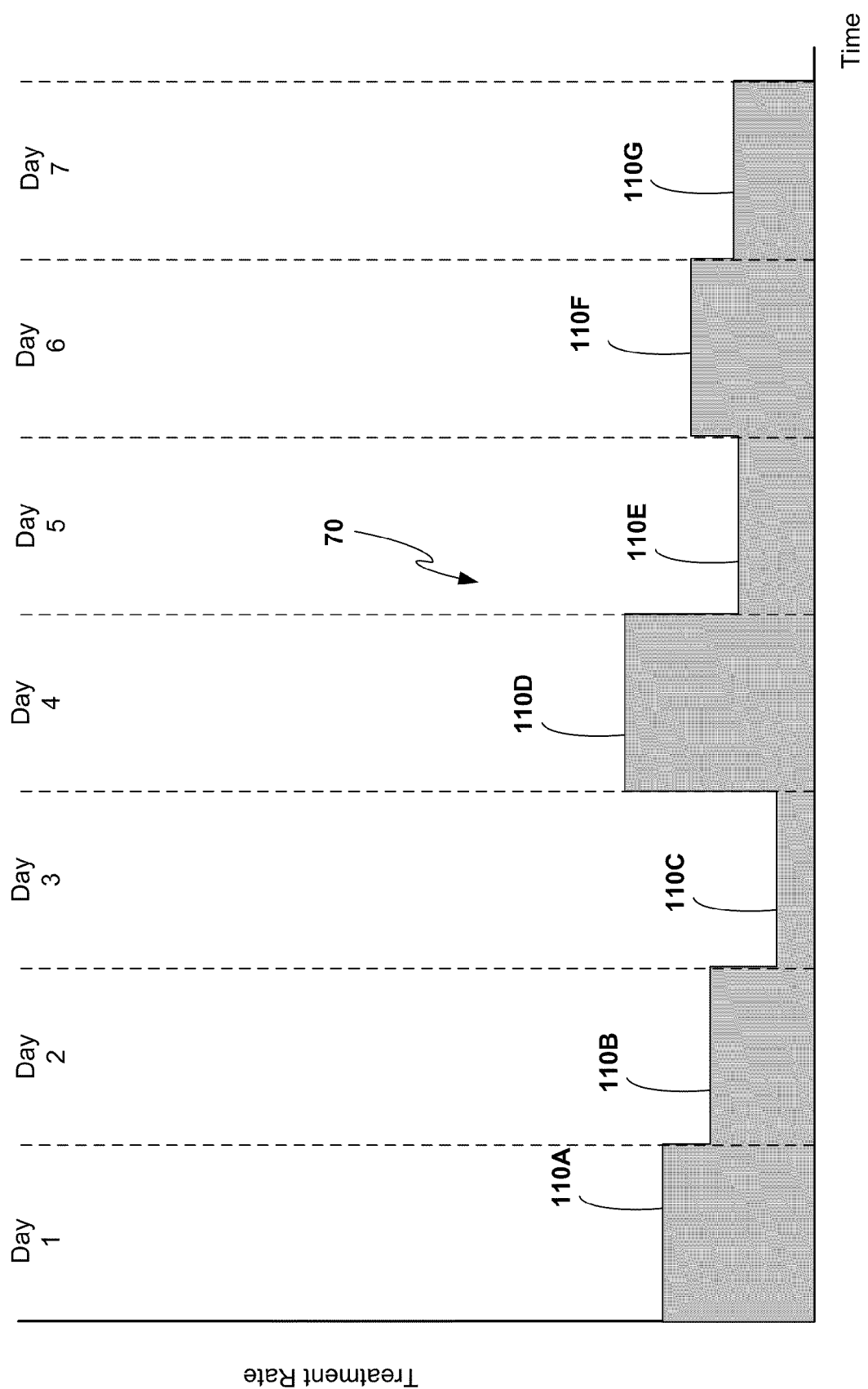
FIG. 9 is a diagram illustrating an example default infusion schedule based on the infusion schedule shown in FIG. 6.

In another example, instead of setting default infusion schedule 70 to one fixed infusion rate over a number of days, the default infusion schedule may include a time-varying schedule such that it approximates a time-varying therapy program 64, while still simplifying the original version of the therapy program to facilitate infusion of a therapeutic amount of the therapeutic agent to patient 1 in the event of an error condition. In one example, an algorithm determines default infusion schedule 70 by determining an average infusion rate for each of a plurality of time periods of infusion schedule 74 and setting default infusion schedule 70 as a series of the time periods with each time period having its own fixed infusion rate equal to the corresponding average infusion rate for that time period. For example, with reference to the example infusion schedule 74 shown in FIG. 6, default infusion schedule 70 may comprise a fixed infusion rate on Day 1 that is set to be equal to the daily average infusion rate 110A for Day 1, a fixed infusion rate on Day 2 set to the daily average infusion rate 110B, a fixed infusion rate on Day 3 set to the daily average infusion rate 110C, a fixed infusion rate on Day 4 set to the daily average infusion rate 110D, a fixed infusion rate on Day 5 set to the daily average infusion rate 110E, a fixed infusion rate on Day 6 set to the daily average infusion rate 110F, and a fixed infusion rate on Day 7 set to the daily average infusion rate 110F. The resulting example default infusion schedule 70 determined by this method is shown in FIG. 9.

In another example, a plurality of flex infusion schedules may be provided for patient 1, for example infusion schedule 72 of FIG. 5 could be provided for the first week of therapy and infusion schedule 74 of FIG. 6 could be provided for the second week of therapy. Alternatively, several different flex infusion schedules could be provided for infusion of the therapeutic agent to patient 1. In the case where a plurality of flex infusion schedules are provided, determining default infusion schedule 70 (92) may include determining a default infusion schedule based on any of the methods described above for each of the flex infusion schedules provided, and then selecting the default infusion schedule having the lowest average infusion rate, a median average infusion rate, or a highest average infusion rate. Selection of a default infusion schedule to use as the default infusion schedule 70 to be saved in backup memory 62 may depend on patient-specific parameters, therapeutic agent-specific parameters, or parameters specific to fluid infusion device 12, such as the parameters described above.

In another example of the method of FIG. 8, determining default infusion schedule 70 (92) may include determining more than one default infusion schedule. For example, a default infusion schedule determination algorithm may be configured to determine a first default infusion schedule including a time-varying schedule, such as the default infusion schedule 70 described above with respect to FIG. 9, and a second default infusion schedule 70 including a fixed default infusion rate, such as a fixed rate set to one of the daily average infusion rates 110 from FIG. 6. In this example, IMD 12 may select the first or the second default infusion schedule based on the type of error condition that is detected. Generally speaking, a first error condition may result in the use of the first default infusion schedule while a second error condition may result in the use of the second default infusion schedule.

In one example, the first default infusion schedule, e.g., the time-varying default infusion schedule, may be used if the error condition does not involves a complete loss of the time point by IMD 12 such that IMD 12 still has at least an approximate sense of the current time, e.g., processor 34 knows when the first error condition occurred and approximately how much time has elapsed since the error condition occurred, within a predetermined period of time. In this situation, IMD 12 is able to keep an accurate account of the passage of time going forward, such that the use of a time-varying default infusion schedule is appropriate. The second default infusion schedule, e.g., a fixed default infusion rate, may be used if the error condition involves a complete loss of the time point by IMD 12 such that the device does not know where in time it is in the infusion schedule currently being executed.

In some examples, rate-selector tables, e.g., stored on processor-controlled memory 36 of IMD 12, may also be provided to determine default infusion schedule 70 in the event of an error condition in the device. The rate-selector tables may comprise one or more continuous rate infusion tables or bolus tables. In one example, the determination of default infusion schedule 70 (90) may be based on one or more values from one or more rate-selector tables. For example, when IMD 12 is programmed, two or more default infusion schedules may be determined, such as by processor 26 of external programmer 20 or by processor 34 of IMD 12, and stored in memory, such as processor-controlled memory 36. The two or more default infusion schedules are referred to collectively herein as a "rate-selector table." Each of the two or more default infusion schedules may be determined by any of the methods described in this disclosure, such as by selecting the minimum infusion rate across a prescribed infusion schedule, an average infusion rate across the infusion schedule, or one or more average rates of portion of the infusion schedule. Processor 34, hardware controller 44, or firmware within IMD 12 may be configured to select one of the two or more default infusion schedules from the rate-selector table. Which of the default infusion schedules that are selected may depend on the type of error condition that is detected and the stage of infusion when the error condition occurred. In one example, each default infusion schedule in the rate-selector table is fixed infusion rate and the default infusion schedule 70 is a fixed default infusion rate that is set at a minimum infusion rate from the rate-selector tables, a maximum infusion rate from the rate-selector tables, a median infusion rate from the rate-selector tables, a modal infusion rate from the rate-selector tables, or an average infusion rate from rate-selector tables.

In addition to therapy program 64, default infusion schedule 70 may, in some examples, be based on an actual delivery history of the therapeutic agent to patient 1, such as the example delivery history 80 (FIG. 7) that shows the delivery of the therapeutic agent to patient 1 over the previous seven days. As described above, example delivery history 80 includes patient-initiated rate changes 82A, 82B and a patient-initiated bolus 84 that patient 1 selects to delivery on top of prescribed infusion schedule 74 from FIG. 6. Delivery history 80 may be used to determine default infusion schedule 70 in much the same way infusion schedule 74 may be used to determine default infusion schedule 70, as described above with respect to FIG. 6.

For example, the average infusion rate 114 for each day of delivery history 80 can be calculated, such as average infusion rate 114A for Day 1, average infusion rate 114B for Day 2, and so on (collectively referred to herein as "daily average infusion rate(s) 114"). As with infusion schedule 74 of FIG. 6, default infusion schedule 70 may based on delivery history 80 by being set as a fixed default infusion rate based on one of the daily average infusion rates 114, such as the minimum daily average infusion rate 114C, the maximum daily average infusion rate 114D, the most common (or modal) daily average infusion rate 114 (none in FIG. 7), or a median daily average infusion rate 114B.

Figure 7:
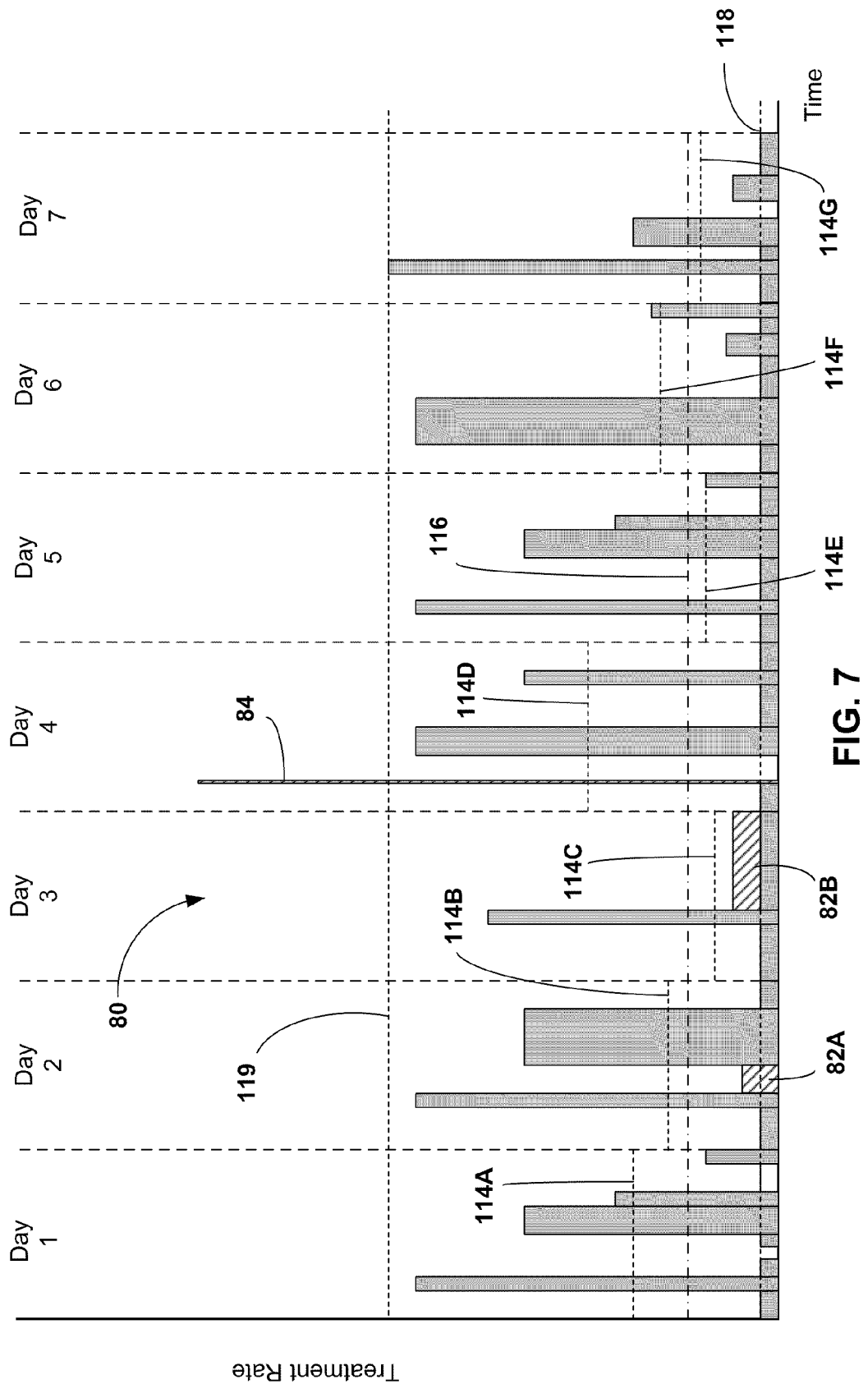
FIG. 7 is a diagram illustrating an example infusion history for the patient who had been prescribed the infusion schedule of FIG. 6.

Default infusion schedule 70 may also be set as a fixed default infusion rate based on the average of the entire delivery history 80, represented by line 116 in FIG. 7, a minimum infusion rate for the entire delivery history 80, represented by line 118, or a maximum infusion rate for the entire delivery history 80, represented by line 119 in FIG. 7. The maximum infusion rate for the entire delivery history may include any patient-initiated rate change 82A, 82B or bolus 84 (not shown in FIG. 7), or may be selected such that patient-initiated infusion are ignored as is the case in the example of FIG. 7. Although the example method described in relation to FIG. 7 describes determining default infusion schedule 70 based on calculations of each day of delivery history 80, such as by determining a daily average infusion rate 114, the infusion patterns of other time periods can be used, such as hourly, every twelve hours, daily, or weekly.

In another example, an aggregate of the programmed infusion schedule, such as infusion schedule 72 or 74, and the delivery history 80, may be used to determine default infusion schedule 70. For example, if it desired to use a minimum daily average infusion rate as the default infusion rate, the average of minimum daily average infusion rate 110C from Day 3 of infusion schedule 74 (FIG. 6) and minimum daily average infusion rate 114C from Day 3 of infusion history 80 may be used as the fixed default infusion rate. The aggregate may be calculated to give more weight to either infusion schedule 74 or to delivery history 80 so that one or the other may have more influence on the final aggregate value or values used for default infusion schedule 70.

In another method of determining default infusion schedule 70 (92), a user determines one or more default infusion schedules for use by IMD 12 in the event an error condition is detected. For example, the user, such as a physician or other clinician, may determine and set the default infusion schedule, such as a fixed default infusion rate, based on characteristics of the patient, such as the therapy program and therapy schedule that has been prescribed for the patient, the patient's history with the therapeutic agent being delivered, and any other factors the user may feel is pertinent to the determination of the default infusion schedule to be followed in the event of an error condition. In another example, the processor, such as processor 26 of external programmer 20 or IMD processor 34, may determine a plurality of default infusion schedules, such as a number of fixed default infusion rates determined by any of the methods described above, whereupon a user, such as a clinician or patient 1, e.g., using external programmer 20, may select one of the fixed default infusion schedules for use by IMD 12 in the event of an error condition. In another example, the user may select the algorithm that will be used to determine the default infusion schedule, such as from a menu of a number of algorithms provided to the user, e.g., via programmer 20.

In another example, determining default infusion schedule 70 (92) may include determining a base infusion schedule and determining a final default infusion schedule that will be stored on backup memory 62 and be used by IMD 12 by adding, subtracting, multiplying, or dividing a rate factor to the base infusion schedule. Generally speaking, the base infusion schedule may be determined by any of the methods described above for determining default infusion schedule 70. The rate factor may be determined based on parameters that are specific to the therapeutic agent, such as side effects that are associated with over infusion or under infusion of the therapeutic agent. For example, if the therapeutic agent is a drug with a higher likelihood of overdose, then a particular rate factor may be subtracted from the base infusion schedule. Examples of this type of therapeutic agent include morphine. In another example, if the therapeutic agent is a drug with adverse effects associated with under infusion, such as severe withdrawal symptoms, than a particular rate factor may be added to the base infusion schedule, for example by increasing the fixed default infusion rate that is determined by an algorithm by a set amount. Examples of this type of therapeutic agent include drugs such as baclofen. The rate factor may also be determined based on parameters that are specific to patient 1, such as condition being treated, patient weight, and patient history with the therapeutic agent or other therapeutic agents. The rate factor may also be determined based on parameters that are specific to IMD 12.

In some therapeutic examples, patient 1 may be switched from treatment with a first fluid having a corresponding first therapy program to treatment with a second fluid having a corresponding second therapy program, also referred to as a bridge condition. The second fluid may be a different therapeutic agent altogether than the first fluid, or the second fluid may be of the same therapeutic agent, but with a different concentration of the therapeutic agent. In either case, e.g., changing the therapeutic agent or changing the concentration of the same therapeutic agent, the first fluid remaining in reservoir 32 is removed, such as by inserting a syringe needle into reservoir 32 to draw the fluid out, but there still remains some fluid in internal channels 46 and catheter 14. The second fluid, e.g., the new therapeutic agent or the fluid having a new concentration of therapeutic agent, is then injected into reservoir 32. A bridge condition may occur, for example, while the second fluid is being removed from reservoir 32 while at least some of the first therapeutic agent is still in the flow path downstream of medical pump 42, such as within internal channels 46 and catheter 14. During the bridge condition, both the first and second fluids may be present in catheter 14, and thus, for a period of time, may both be infused into patient 1.

The bridge condition may be considered to continue until the first fluid has been emptied from the downstream flow path. In one example, the first fluid is assumed to be emptied from the downstream flow path when a predetermined volume of the second fluid has been pumped by medical pump 42, such as a volume equal to the volume of the downstream flow path or some multiple thereof, such as between about 1 and about 3 times the volume of the downstream flow path, for example about 2 times the downstream flow path. In another example, the first fluid is considered to be emptied from the downstream flow path after a predetermined period of time has elapsed, wherein the predetermined time is the time it is expected that it will take for the first fluid to be pumped out of the downstream flow path. The predetermined period of time can be determined based on an expected average infusion rate during the bridge condition.

In one example including a bridge condition, determining default infusion schedule 70 (92) may include determining a first default infusion schedule for the first fluid, determining a second default infusion schedule for the second fluid, and selecting either the first default infusion schedule or the second default infusion schedule to be the default infusion schedule during the bridge condition. For example, the default infusion schedule for each fluid may be stored in memory, such as in a rate-selector table in processor-controlled memory 36, wherein processor 34, hardware controller 44, or firmware within IMD 12 may be configured to select one of the default infusion schedules from the rate-selector table to use based on wherein IMD 12 believes it is in the bridge condition. After the first fluid is withdrawn from reservoir 32 and the second fluid is injected into reservoir 32, the second therapy program and the second default infusion schedule corresponding to the second fluid may be sent to IMD 12, such as via telemetry module 38. In one example, the volume of the first fluid that remains in the downstream flow path is determined based on the known length of interior channels 46 and catheter 14 and processor 34 or hardware controller 44 keeps track of the amount of the second fluid being delivered by medical pump 42 to determine if the volume of the first fluid has been delivered. If an error condition occurs before the volume of the first fluid in the downstream flow path has been delivered, then processor 34 or hardware controller 44 will use the first default infusion schedule of the first fluid until the remainder of the volume of the first fluid in downstream flow path is delivered. At that point, processor 34 or hardware controller 44 will switch to using the second default infusion schedule.

In another example, when the second fluid is injected into reservoir 32, a time stamp is sent to IMD 12, such as via telemetry module 38, for storage in memory, such as processor-controlled memory 36 or hardware-controlled memory 56. The time stamp indicates the amount of time that is expected to be required to pump the first fluid out of the downstream flow path. Upon detection of an error condition that causes IMD 12 to transition to using a default infusion schedule during the bridge condition, IMD 12 uses the time stamp to determine which of the first default infusion schedule (for the first fluid) or the second default infusion schedule (for the second fluid) will be used at a particular point in time. The first default infusion schedule is used to direct infusion by medical pump 42 up until the time stamp. After the time stamp is reached, the second default infusion schedule is used.

In another example, determining default infusion schedule 70 (92) may include determining a bridge default infusion schedule that is based on some combination of the first default infusion schedule for the first fluid and the second default infusion schedule for the second fluid. The bridge default infusion schedule may be selected to be the more conservative of the first default infusion schedule and the second default infusion schedule. The "more conservative" of the first and the second default infusion schedules may be a function of various parameters specific to the first and second fluids, such as side effects that are associated with over infusion or under infusion of each fluid.

Parameters that may be used to determine the "more conservative" of the first and second default infusion schedules may be specific to patient 1, such as condition being treated, patient weight, and patient history with each fluid. For example, if both the first fluid and the second fluid involve adverse side effects associated with under infusion with relatively little risk of an overdose due to over infusion, then the one of the first or the second default infusion schedule having the larger overall output, e.g., the amount of therapeutic agent that would be infused into patient 1 over the entirety of the default infusion schedule, may be selected to be the bridge default infusion rate to avoid patient 1 experiencing side effects of under infusion of either the first or second fluid. In another example in which one or both of the first fluid and the second fluid have risks associated with over infusion, then the one of the first or the second default infusion schedule having the lower overall output may be selected as the bridge default infusion schedule to avoid the side effects associated with over infusion.

In another example of determining a bridge default infusion schedule as part of determining default infusion schedule 70 (92) in the method of FIG. 8, the bridge default infusion schedule may be calculated based on both the first default infusion schedule and the second default infusion schedule, such as by averaging the two schedules or by giving weight to agent-specific factors such as the side effects associated with over infusion and under infusion of the first and second therapeutic agents. For example, if the first default infusion schedule for the first therapeutic agent is a fixed default infusion rate of 15 mcg/hour and the second default infusion schedule of the second therapeutic agent is a fixed default infusion rate of 20 mcg/hour, the default infusion rate during the bridge condition may be set at 15 mcg/hour, e.g., the lower of the two rates, at 20 mcg/hour, e.g., the higher of the two rates, at 17.5 mcg/hour, e.g., the average of the two rates, or somewhere else between 15 and 20 mcg/hour depending on the particular therapeutic agents involved.

Referring again to the example method of FIG. 8, in addition to determining default infusion schedule 70 (92), the method includes storing the default infusion schedule 70 on backup memory 62 of IMD 12 (96). Storing the default infusion schedule 70, such as on backup memory 62 (96) may include any one of several storage configurations. In the example shown in FIG. 2, storing default infusion schedule 70 (96) includes storing the default infusion schedule 70 in backup memory 62 included in processor-controlled memory 36. In other examples, storing default infusion schedule 70 (96) in the method of FIG. 8 may include any of the various storage configurations illustrated in and described above with reference to FIGS. 3 and 4 including storage on backup memory 62A of RAM 52 or backup memory 62B of flash memory 54 of processor-controlled memory 36 in the example of FIG. 3, as well as storage on backup memory 62B of hardware registers 58 of hardware-controlled memory 56 in the example of FIG. 4.

In addition to storing default infusion schedule 70 on backup memory 62 of IMD 12 (96), the method of FIG. 8 includes determining if an error condition is present in IMD 12 (98). Determining if an error condition is present (98) may, generally speaking, be performed by processor 34, hardware controller 44, or both. As described above, in some examples, processor 34 may be configured to recognize error conditions such as corruption of therapy program 64, other memory corruption that affects delivery of therapeutic agent, loss of time point by processor 34, pump software errors, pump reset, and the like, and hardware controller 44 may be configured to recognize error conditions in which processor 34 itself or pump software are malfunctioning.

In the event that an error condition is detected, e.g., by processor 34 of IMD 12, the method of FIG. 8 includes delivering the therapeutic agent to patient 1 according to default infusion schedule 70 (100) in order to maintain infusion of at least a minimum therapeutic amount of the therapeutic agent to patient 1 until a physician or other clinician is able to reprogram IMD 12. Delivery of the therapeutic agent to patient 1 according to default infusion schedule 70 (100) may be directed by processor 34 or hardware controller 44. In one example, wherein the error condition is such that processor 34 is still able to control infusion by medical pump 42, then processor 34 may access default infusion schedule 70 from backup memory 62 and may direct hardware controller 44 to deliver the therapeutic agent according to default infusion schedule 70. In another example, wherein the error condition is one wherein processor 34 or pump software is malfunctioning, hardware controller 44 may access default infusion schedule 70 from backup memory 62 and control medical pump 42 accordingly.

In yet another example, hardware controller 44 is responsible for directing delivery of the therapeutic agent according to default infusion schedule 70 regardless of which type of error condition is detected. If hardware controller 44 detects the error condition, it accesses default infusion schedule 70 from backup memory 62 and control medical pump 42 accordingly. If processor 34 detects the error condition, it communicates the detection of the error condition to hardware controller 44, which then directs delivery of the therapeutic agent according to default infusion schedule 70. One example of a method of communicating the error condition from processor 34 to hardware controller 44 includes communication through a specific protocol, such as writing to hardware-controlled memory 56 or a more robust messaging scheme between processor 34 and hardware controller 44. Another example may be stopping communication or ceasing an exchange of signal, e.g., if there is a watchdog or beacon or message exchange between processor 34 and hardware controller 44 that is occurring on a regular basis which is then stopped by processor 34. In yet another example, a log type-supplementary communication is provided by which processor 34 provides hardware controller 44 with information regarding what type of error condition was detected so that hardware controller 44 may use a default infusion schedule that is a proper response to the error condition detected.

Figure 10:
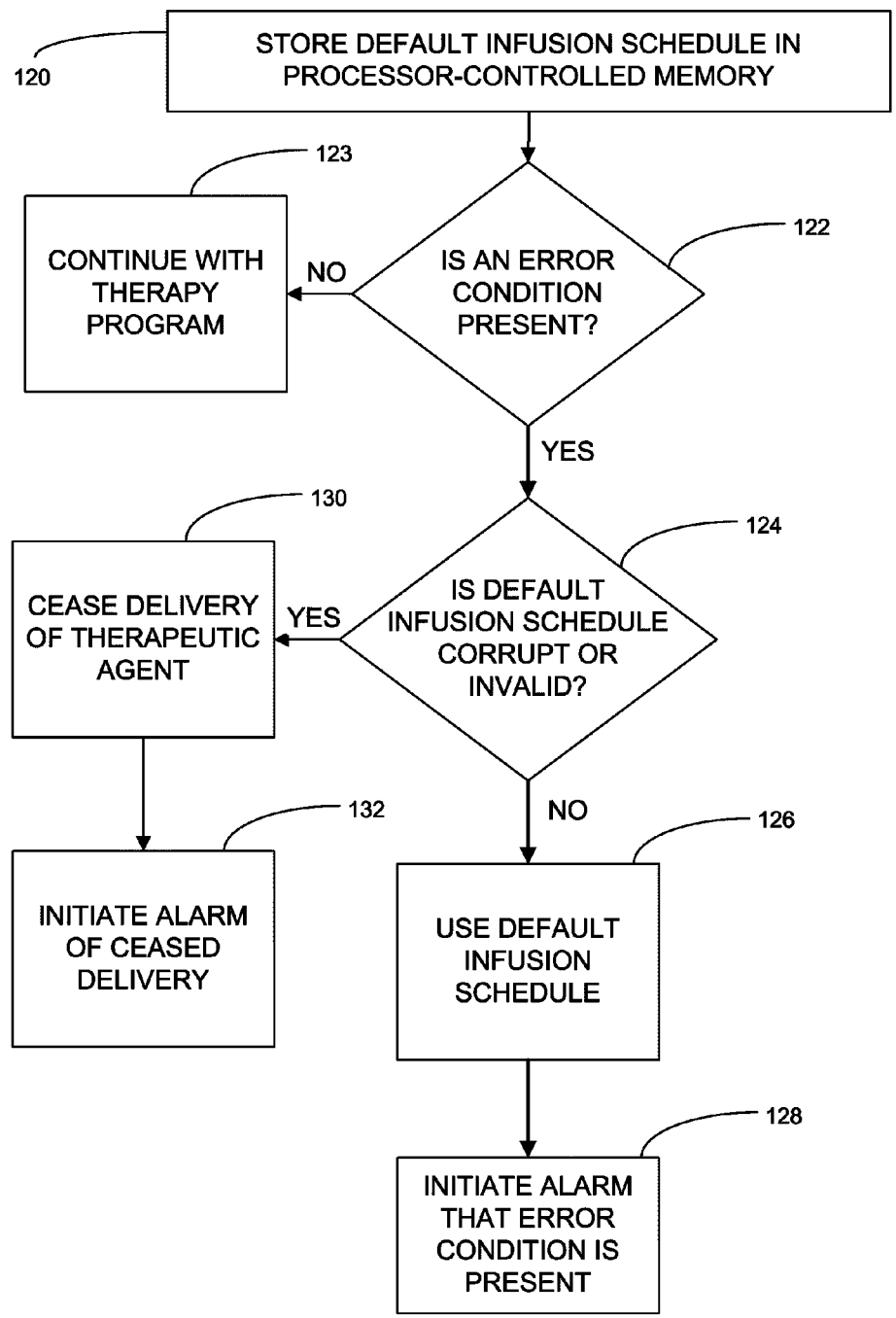
FIG. 10 is a flowchart showing a first example method of storing the default infusion schedule in a backup memory and detecting an error condition within an implantable fluid delivery device.

FIG. 10 is a flowchart illustrating a first example method of storing a default infusion schedule in a backup memory of an IMD and detecting an error condition within an IMD. The example method of FIG. 10 may be executed in whole or in part by one or more of processor 34 or hardware controller 44 of IMD 12, processor 26 of programmer 20, or a processor of another device. The example method of FIG. 10 includes storing default infusion schedule 70 in processor-controlled memory 36 of IMD 12 (120), and determining if an error condition exists in IMD 12 (122), such as by detecting that therapy program 64 is corrupt in main memory 60 or determining that processor 34 has lost time point. If no error condition exists, IMD 12 continues to use the prescribed therapy program 64 to deliver therapy to patient 1 (123).

If an error condition does exist, default infusion schedule 70 is verified as uncorrupted and valid in backup memory 62 (124). If default infusion schedule 70 is found to be uncorrupted and valid, IMD 12 employs default infusion schedule 70 to direct delivery of the therapeutic agent to patient 1 (126). The method may also optionally include triggering an alarm (128) when an error condition is detected. For example, IMD 12 may include an audible or vibratory alarm device 49 (FIG. 2) that immediately alerts patient 1 that an error condition was detected and that default infusion schedule 70 is being used. An example alarm device 49 may include a sound system, such as a piezoelectric device, that is activated by processor 34 or hardware controller 44 upon detection of the error condition and use of default infusion schedule 70. Alarming may also include displaying an alarm message on external programmer 20 or another device in communication with IMD 12 or programmer 20 to alert patient 1 or another user, such as a clinician, of the existence of the error condition or the use of default infusion schedule 70. If default infusion schedule 70 is found to be corrupt or invalid for some other reason, IMD 12 ceases delivery of the therapeutic agent (130) and initiates an alarm (132), such as by processor 34 or hardware controller 44 instructing medical pump 42 to stop delivery of the therapeutic agent and delivering an alarm message via telemetry module 38 to external programmer 20.

Alarms associated with the example method of FIG. 10, as well as any other methods described in this disclosure, may be triggered by processor 34 or hardware controller 44 of IMD 12 or a processor of another device, e.g., processor 26 of programmer 20, and may generally include audible, tactile, and/or visual alerts. For example, an error condition detection alarm may include audible alerts issued by programmer 20 or another external device associated with therapy system 10. In another example, the triggered alarm includes IMD 12 vibrating within the body of patient 1, thereby providing a tactile alert. In another example, processor 34 or hardware controller 44 may be configured to prompt external programmer 20, or another device incorporated in or communicatively connected to IMD 12, to provide an alert message to patient 1 or a clinician, such as by providing an audio or visual alert. In one example, IMD 12 or programmer 20 may be configured to be in communication with a monitoring or relaying device, such as a home monitor within the patient's home, wherein the monitoring or relaying device is in communication with a monitoring station, such as within a clinic or hospital that is monitored by a clinician, through a network, such as the internet, a LAN, a WAN, a PSTN, or a cellular telephone network. Other alert messages may include text or graphical messages delivered to patient 1 and/or a clinician via text message or e-mail from programmer 20 or another electronic device communicatively connected to IMD 12 and/or programmer 20.

Figure 11:
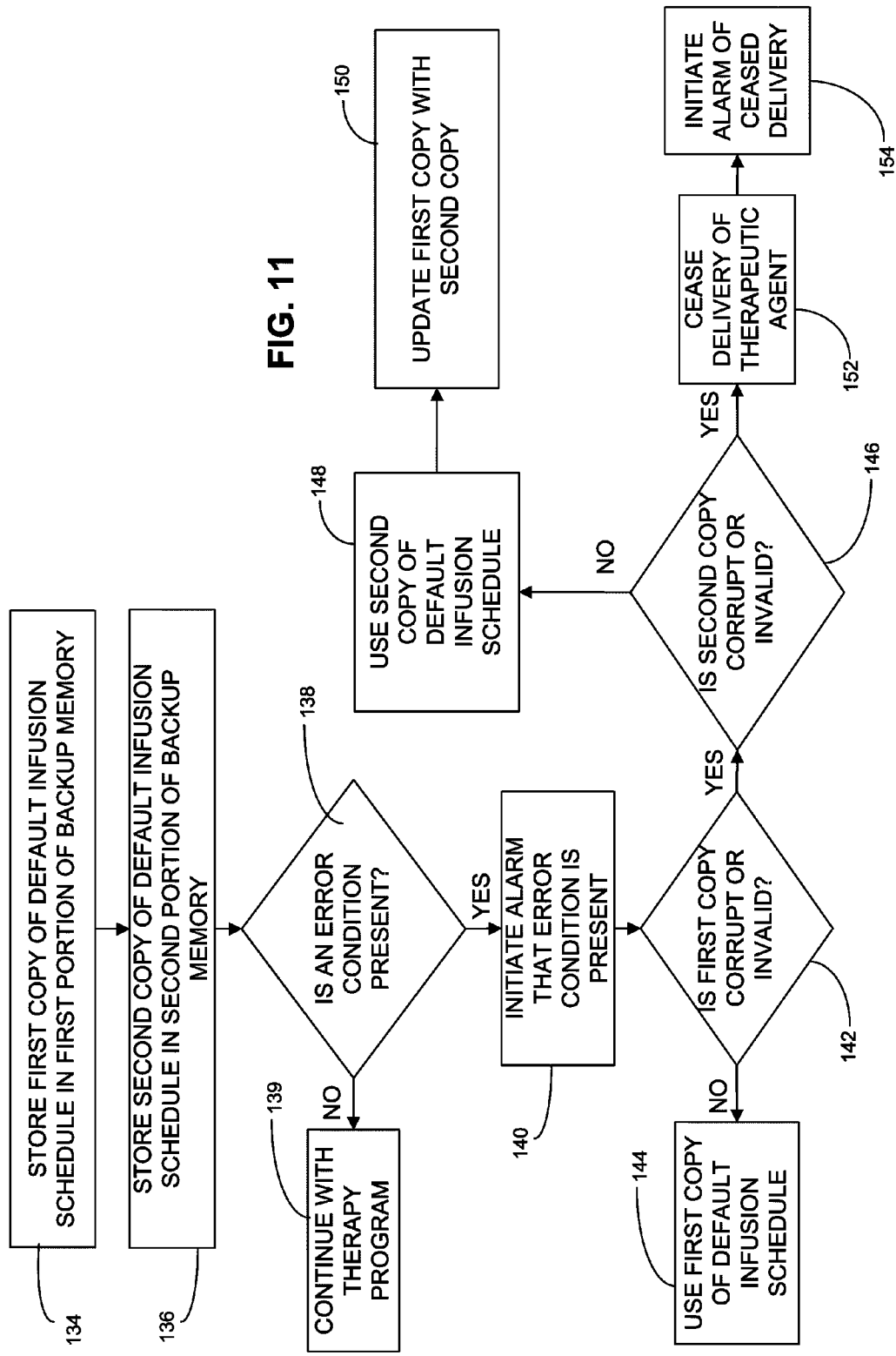
FIG. 11 is a flowchart showing a second example method of storing the default infusion schedule in a backup memory and detecting an error condition within an implantable fluid delivery device.

Another example method of storing default infusion schedule 70 and detecting error conditions within IMD 12 is illustrated in the flow chart of FIG. 11. The method of FIG. 11 includes storing a first copy of the default infusion schedule 70 in a first portion of backup memory 62 that is a portion of processor-controlled memory 36 (134) and redundantly storing a second copy of default infusion schedule 70 in a second portion of backup memory 62 that is a portion of processor-controlled memory 36 (136). Storing the first copy of default infusion schedule 70 (134) may include, e.g., storing a first copy of default infusion schedule 70A in backup memory portion 62A of RAM 52, as illustrated in the example of FIG. 3. Redundantly storing a second copy of default infusion schedule 70 (136) may include, e.g., storing a second copy of default infusion schedule 70B in backup memory portion 62B of flash memory 54, as also illustrated in FIG. 3. Additional copies of the default infusion schedule may be stored in other areas of main memory 60 or backup memory 64, such as third, fourth, and fifth copies of the default infusion schedule in third, fourth, and fifth portions of backup memory.

After storing a first copy (134) and redundantly storing a second copy (136), the example method of FIG. 11 includes determining if an error condition is present in IMD 12 (138). If no error condition is present, IMD 12 continues to use prescribed therapy program 64 (139). If an error condition is present, the example method of FIG. 11 includes initiating an alarm indicating that an error condition is present (150).

IMD may also be configured so that whenever default infusion schedule 70 is updated or changed, all locations of backup memory 62 where copies of default infusion schedule 70 are stored are synchronized and updated substantially simultaneously. The synchronized and substantially simultaneous updating may be based on any technique available for synchronizing and guaranteeing data update and integrity that may be stored in various memory locations.

Continuing with FIG. 11, the example method includes determining if first copy of default infusion schedule 70A is uncorrupted in backup memory 62A and valid (142), which may be performed by processor 34. If first copy of default infusion schedule 70A is uncorrupted and valid, IMD 12 uses first copy 70A to direct infusion of the therapeutic agent (144). If first copy 70A is found to be corrupted or invalid for some other reason, then IMD 12, e.g., using processor 34, will determine if second copy of default infusion schedule 70B is uncorrupted and valid (146). If second copy 70B is found to be uncorrupted and valid, then IMD 12 will use second copy 70B of default infusion schedule 70 to direct infusion of the therapeutic agent (148). IMD 12 may also update first copy 70A in first portion of backup memory 62A with the uncorrupted and valid second copy 70B (150), and then use either the original second copy 70B or the updated first copy 70A to direct infusion of the therapeutic agent (148). If second copy 70B is found to also be corrupt or invalid for some other reason, the example method of FIG. 11 may include ceasing delivery of the therapeutic agent (152) and initiating an alarm (154), such as by processor instructing medical pump 42 to stop delivery of the therapeutic agent and delivering an alarm message to external programmer 20. The method may also include periodically checking the first copy 70A and second copy 70B to determine if either copy is corrupted or invalid, and upon determining that one of the copies is corrupted or invalid, copying the uncorrupted and valid copy to replace and update the corrupted or invalid copy.

Figure 12:
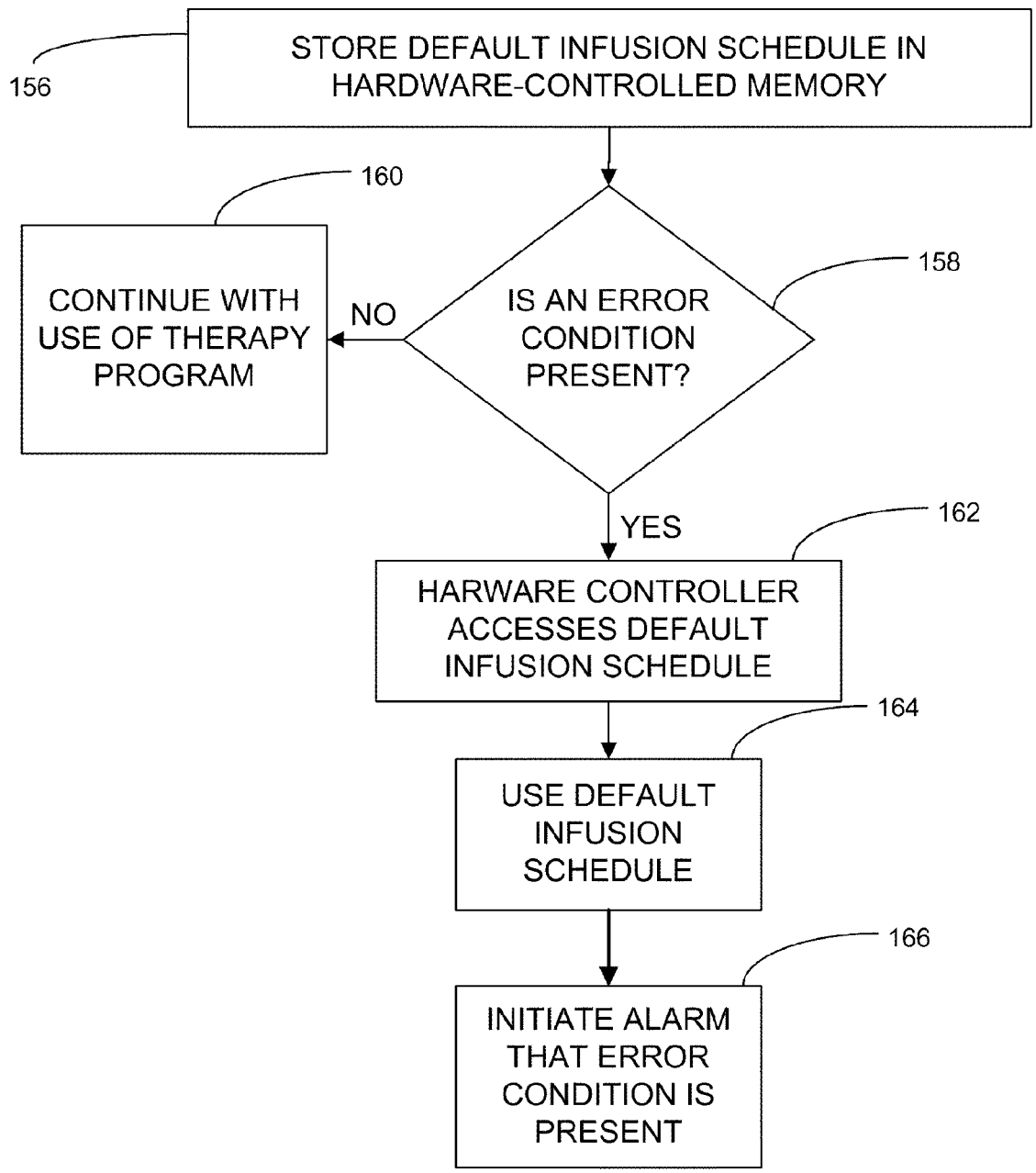
FIG. 12 is a flowchart showing a third example method of storing the default infusion schedule in a backup memory and detecting an error condition within an implantable fluid delivery device.

Yet another example method of storing default infusion schedule 70 and detecting error conditions within IMD 12 is illustrated in the flow chart of FIG. 12. The example method of FIG. 12 includes storing default infusion schedule 70 on a hardware-controlled memory 56 (156), such as in hardware registers 58 shown in FIG. 2. The example method of FIG. 12 further includes hardware controller 44 determining that an error condition wherein processor 34 or IMD software are malfunctioning (158) such that delivery of the therapeutic agent under therapy program 64 is no longer being followed. Examples of such error conditions are described above and include a failure in the communication between processor and hardware controller 44, e.g., an improper handshake, or a failure of a crosschecking mechanism between hardware and software of fluid delivery device 12, such as an incorrect strobing of a watchdog timer. The example method of FIG. 12 may also include processor 34 detecting the error condition, such as finding therapy program 64 or regular infusion schedule 72, 74 corrupt in memory, loss of time point by processor 34, IMD software errors (errant pointers, memory corruption, stack overflow, etc.), or pump reset, and communicating with hardware controller 44 the detection of the error condition by processor 34. After receiving the communication from processor 44, hardware controller 44 then proceeds as if it had detected the error condition by accessing default infusion schedule 70 (162) and using default infusion schedule 70 for the delivery of the therapeutic agent (164).

If no error condition is present, hardware controller 44 continues following instructions from processor 34 and delivering prescribed therapy program 64 (160). If such an error condition does exist, the example method includes hardware controller 44 accessing default infusion schedule 70 directly from hardware-controlled memory 56 (162), and hardware controller 44 using default infusion schedule 70 to maintain infusion of the therapeutic agent to patient 1 (164). The example method of FIG. 12 may also include hardware controller 44 initiating an alarm indicating the error condition is present (166), such as by activating an internal alarm device 49 (FIG. 2) or transmitting an alarm signal to programmer 20 via telemetry module 38.

Figure 13:
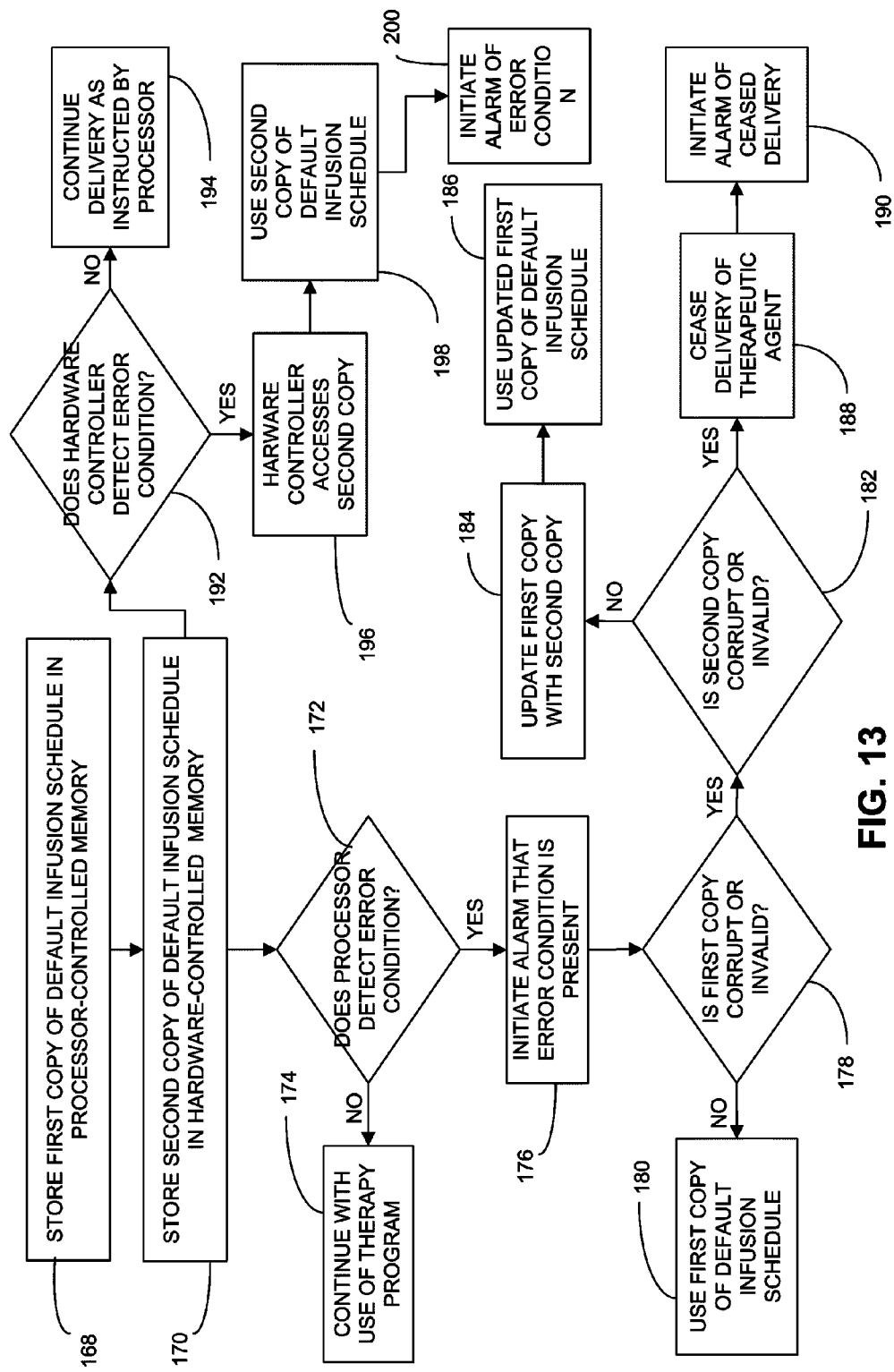
FIG. 13 is a flowchart showing a fourth example method of storing the default infusion schedule in a backup memory and detecting an error condition within an implantable fluid delivery device.

Another example method of storing default infusion schedule 70 and detecting error conditions within IMD 12 is illustrated in the flow chart of FIG. 13. The example method of FIG. 13 includes storing a first copy of default infusion schedule 70 on a processor-controlled memory 36 (168) and storing a second copy of default infusion schedule 70 on a hardware-controlled memory 56 (170). Storing the first copy of default infusion schedule 70 (168) may include, e.g., storing first copy of default infusion schedule 70A in a backup memory portion 62A of flash memory 54, as illustrated in FIG. 4. Storing a second copy of default infusion schedule 70 (170) may include, e.g., storing a second copy of default infusion schedule 70B in a backup memory portion 62B of hardware registers 58, also as illustrated in FIG. 4.

Continuing with FIG. 13, the example method further includes processor 34 determining if an error condition wherein therapy program 64 stored in main memory 60 should not be used (172), but wherein processor 34 is otherwise functioning properly. Examples of such an error condition are described above and include therapy program 64 being corrupted, a loss of time point, IMD software errors (errant pointers, memory corruption, stack overflow, etc.), or pump reset. If no such error condition is present, processor 34 may direct that IMD 12 continue with use of prescribed therapy program 64 (174). If processor 34 determines that such an error condition is present, processor 34 may initiate an alarm indicating the error condition is present (176). Next, the example method of FIG. 13 includes determining if first copy of default infusion schedule 70B is uncorrupted and valid (178).

If first copy 70A is uncorrupted and valid, processor 34 may use first copy 70A to direct infusion of the therapeutic agent (180). If first copy 70A stored on processor-controlled memory 36 is found to be corrupted or invalid for some other reason, then processor 34 may access second copy of default infusion schedule 70B and determine if second copy 70B is uncorrupted and valid (182). If second copy 70B is found to be uncorrupted and valid, then processor 34 may update the corrupted or invalid first copy 70A with second copy 70B (184), and use updated first copy 70A to direct infusion of the therapeutic agent (186). Processor 34 may also use second copy 70B directly to direct infusion of the therapeutic agent, rather than updating first copy 70A with second copy 70B and then using updated first copy 70A. If second copy 70B is also found to be corrupt or invalid, then processor 34 may direct that IMD 12 cease delivery of the therapeutic agent (188) and initiate an alarm that delivery of the therapeutic agent has ceased (190).

Continuing with the example method of FIG. 13, at the same time that processor 34 is determining whether an error condition exists wherein therapy program 64 stored in main memory 60 should be used (172), hardware controller 44 determines if an error condition exists wherein processor 34 or IMD software are malfunctioning (192). Examples of such an error condition are described above and include a failure in the communication between processor and hardware controller 44 or a failure of a crosschecking mechanism between hardware and software of IMD 12. If hardware controller 44 determines that such an error condition does not exist, than hardware controller 44 continues following instructions from processor 34 regarding delivery of the therapeutic agent (194). If hardware controller 44 determines that processor 34 or IMD software are malfunctioning, hardware controller 44 accesses second copy 70B of default infusion schedule 70 directly from hardware-controlled memory 56 (196), and hardware controller 44 uses second copy of default infusion schedule 70B to maintain infusion of the therapeutic agent to patient 1 (198). The example method of FIG. 13 may also include initiating an alarm (200) that hardware controller 44 detected an error condition wherein processor 34 or IMD software are malfunctioning and uses second copy of default infusion schedule 70B. The method may also include periodically checking the first copy 70A and second copy 70B to determine if either copy is corrupted or invalid, and upon determining that one of the copies is corrupted or invalid, copying the other uncorrupted and valid copy to replace and update the corrupted or invalid copy.

Turning back to the example method of FIG. 8, determining that an error condition exists in IMD 12 (98), may include processor 34 detecting the error condition and determining that IMD 12 cannot, or should not, continue to use therapy program 64. Examples of error conditions that may be detectable by processor 34 include corruption of the regular therapy program found by processor 34 within main memory 60; a loss of the time point that processor 34 needs to delivery therapy program 64, such as if therapy program 64 comprises a weekly or daily schedule and the IMD software loses the current time and/or day of the week; IMD software errors that cause a reinitialization upon which processor 34 cannot deliver a time-varying therapy program, such as errant pointers, memory corruption, stack overflow, or logic errors; error or inconsistencies discovered during execution of therapy program 64, such as incorrect, inconsistent, or invalid parameters; and an unplanned reset by IMD 12, which may make delivery of programmed therapy program 64 undesirable, particularly for a time-varying therapy program 64.

Determining that an error condition exists in IMD 12 (98) may also include hardware controller 44 determining that processor 34 or IMD software are malfunctioning such that continuing to follow instructions from processor 34 may be undesirable. Examples of error conditions that hardware controller 44 may detect that would indicate such a malfunction may include a failure in the timing or another defined parameter of the communication between processor and hardware controller 44, such as a improper handshake, or a failure of a crosschecking mechanism between hardware and software of IMD 12, such as an incorrect strobing of a watchdog timer.

Determining that an error condition exists in IMD 12 (98) may also include processor 34 detecting an error condition, such as corruption of therapy program 64 in memory, loss of time point, IMD software errors (errant pointers, memory corruption, stack overflow, or logic errors), error or inconsistencies discovered during execution of therapy program 64, or an unplanned reset, and communicating with hardware controller 44 that the error condition is present and instructing hardware controller 44 to deliver according to default infusion schedule 70.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g., sacral, pudendal or perineal nerves, organs, muscles, or muscle groups. In one example, a catheter may be positioned to deliver a therapeutic fluid to a deep brain site or within the heart or blood vessels. In another example, a catheter may be positioned to deliver therapeutic fluid to the liver or lower torso vascular area.

Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure, including those attributed to processor 34 and hardware controller 44 of IMD 12 and processor 26 in external programmer 20 may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

This disclosure refers to illustrative examples that are not meant to be construed in a limiting sense. Various modifications of the illustrative examples, as well as additional examples in line with the disclosure, will be apparent to persons skilled in the art upon reference to this description. Any specific numerical value or range described in the foregoing disclosure shall not be limiting, except for values or ranges included in the following claims.

The invention claimed is:

1. A fluid delivery system comprising:
   a pump configured to deliver a therapeutic agent to a patient;
   a memory storing a therapy program defining the delivery of the therapeutic agent to the patient by the pump and a default infusion schedule based on the therapy program; and
   a processor configured to control the pump to deliver the therapeutic agent to the patient according to the therapy program, to determine an error condition that prevents the pump from continuing to deliver therapy according to the therapy program, and, upon determination of the error condition, to control the pump to deliver the therapeutic agent to the patient according to the default infusion schedule.

2. The system of claim 1, wherein the error condition comprises at least one of corruption of the therapy program stored in the memory, loss of a time point, a pump software error, a pump reset, an error in infusion parameters within the therapy program, a perceived malicious attempt by an external device, or a pump stoppage having a duration longer than a predetermined time.

3. The system of claim 2, wherein the pump software error comprises at least one of an errant pointer, memory corruption, a stack overflow, an unexpected code execution, a memory allocation failure, an inter-processor communication failure, or a software exception.

4. The system of claim 2, further comprising a time-measuring device, wherein the loss of time point comprises the time-measuring device becoming unable to reliably measure the passage of time.

5. The system of claim 4, further comprising a second time-measuring device, wherein the first time-measuring device cross-checks time measurement with the second time-measuring device, wherein the loss of time point comprises both the first time-measuring device and the second time measuring device becoming unable to reliably measure the passage of time.

6. The system of claim 1, wherein the processor is a hardware-based controller, the system further comprising a pump software processor.

7. The system of claim 6, wherein the error condition comprises at least one of a malfunction by the pump software processor, a communication error between the hardware-based controller and the pump software processor, an improper handshake between the hardware-based controller and the pump software processor, or improper strobing of a watchdog timer associated with the hardware-based controller.

8. The system of claim 1, wherein the memory comprises at least one of read-only memory (ROM), random access memory (RAM), non-volatile RAM (NVRAM), electrically erasable programmable read-only memory (EEPROM), flash memory, or hardware registers.

9. The system of claim 1, wherein the memory comprises a first processor-controlled portion and a second processor-controlled portion, wherein the therapy program is stored on the first processor-controlled portion and the default infusion schedule is stored on the second processor-controlled portion.

10. The system of claim 1, wherein the memory comprises a processor-controlled portion and a hardware-controlled portion, wherein the therapy program is stored on the processor-controlled portion and the default infusion schedule is stored on the hardware-controlled portion.

11. The system of claim 1, wherein a first copy of the default infusion schedule is stored in a first portion of the memory and a second copy of the default infusion schedule is stored in a second portion of the memory.

12. The system of claim 11, wherein the first portion of the memory is a processor-controlled memory and the second portion of the memory is a processor-controlled memory.

13. The system of claim 11, wherein the first portion of the memory is a processor-controlled memory and wherein the second portion of the memory is a hardware-controlled memory.

14. The system of claim 11, wherein the first portion of the memory comprises a first type of memory and the second portion of the memory comprises a second type of memory.

15. The system of claim 14, wherein the first type of memory comprises at least one of read-only memory (ROM), random access memory (RAM), non-volatile RAM (NVRAM), electrically erasable programmable read-only memory (EEPROM), or flash memory.

16. The system of claim 14, wherein the second type of memory comprises at least one of read-only memory (ROM), random access memory (RAM), non-volatile RAM (NVRAM), electrically erasable programmable read-only memory (EEPROM), flash memory, or hardware registers.

17. The system of claim 1, wherein the therapy program comprises a therapy infusion schedule and the default infusion schedule is determined based on the therapy infusion schedule.

18. The system of claim 17, wherein the therapy infusion schedule comprises a fixed infusion rate and the default infusion schedule comprises a fixed default infusion rate equal to the fixed infusion rate of the therapy infusion schedule.

19. The system of claim 17, wherein the therapy infusion schedule comprises a time-varying infusion schedule.

20. The system of claim 19, wherein the default infusion schedule is a fixed default infusion rate that is equal to at least one of:
   an average infusion rate of the time-varying infusion schedule;
   a minimum infusion rate of the time-varying infusion schedule;

a maximum infusion rate of the time-varying schedule;
an average infusion rate for a portion of the time-varying infusion schedule;
a minimum average infusion rate from a set of average infusion rates for a plurality of portions of the time-varying infusion schedule;
a median average infusion rate from a set of average infusion rates for a plurality of portions of the time-varying infusion schedule;
a modal average infusion rate from a set of average infusion rates for a plurality of portions of the time-varying infusion schedule;
a maximum average infusion rate from a set of average infusion rates for a plurality of portions of the time-varying infusion schedule;
a minimum infusion rate in a rate-selector table of the pump stored on the memory;
a maximum infusion rate in a rate-selector table of the pump stored on the memory;
a median infusion rate in a rate-selector table of the pump stored on the memory;
a modal infusion rate in a rate-selector table of the pump stored on the memory;
an average infusion rate in a rate-selector table of the pump stored on the memory;
an average infusion rate of an infusion history of the patient;
a minimum infusion rate of an infusion history of the patient;
a maximum infusion rate of an infusion history of the patient;
an average infusion rate for a portion of an infusion history of the patient;
a minimum average infusion rate from a set of average infusion rates for a plurality of portions of an infusion history of the patient;
a maximum average infusion rate from a set of average infusion rates for a plurality of portions of an infusion history of the patient;
a median average infusion rate from a set of average infusion rates for a plurality of portions of an infusion history of the patient; or
a modal average infusion rate from a set of average infusion rates for a plurality of portions of an infusion history of the patient.

21. The system of claim 1, wherein the processor is a first processor, the system further comprising an external programmer comprising a second processor, the second processor of the external programmer being configured to determine the default infusion schedule based on the therapy program, wherein the external programmer is configured to transmit the therapy program and the default infusion schedule to an implantable fluid delivery device for storage in the memory.

22. The system of claim 1, wherein the processor is configured to determine the default infusion schedule based on the therapy program.

23. The system of claim 22, wherein the processor is configured to determine the default infusion schedule by software instructions running on the processor.

24. The system of claim 1, further comprising a hardware module for determining the default infusion schedule based on the therapy program.

25. The system of claim 24, wherein the hardware module is a hardware-based controller for controlling the pump.

26. The system of claim 1, further comprising an alarm device configured to provide an alert upon determination of the error condition or delivery of the therapeutic agent to the patient according to the default infusion schedule.

27. A method comprising:
determining a default infusion schedule based on a therapy program that defines delivery of a therapeutic agent to a patient by an implantable fluid delivery device;
storing the default infusion schedule on a memory of the implantable fluid delivery device;
determining if an error condition is present in the implantable fluid delivery device such that the device cannot continue delivering therapy according to the therapy program; and
if the error condition is present, delivering the therapeutic agent according to the default infusion schedule.

28. The method of claim 27, further comprising determining the therapy program before determining the default infusion schedule.

29. The method of claim 27, wherein determining the default infusion schedule is performed by a processor of an external programmer, the method further comprising transmitting the default infusion schedule from the external programmer to the implantable fluid delivery device.

30. The method of claim 27, wherein determining the default infusion schedule is performed by a user.

31. The method of claim 30, wherein the user is a clinician who determines the default infusion schedule based on characteristics of the patient.

32. The method of claim 27, wherein determining the default infusion schedule comprises a processor determines a plurality of default infusion schedules and a user selecting one of the plurality of default infusion schedules determined by the processor.

33. The method of claim 27, wherein determining the default infusion schedule comprises determining a fixed default infusion rate based on a time-varying therapy infusion schedule of the therapy program.

34. The method of claim 33, wherein determining the fixed default infusion rate comprises setting the fixed default infusion rate at least one of:
an average infusion rate of the time-varying infusion schedule;
a minimum infusion rate of the time-varying infusion schedule;
a maximum infusion rate of the time-varying schedule;
an average infusion rate for a portion of the time-varying infusion schedule;
a minimum average infusion rate from a set of average infusion rates for a plurality of portions of the time-varying infusion schedule;
a median average infusion rate from a set of average infusion rates for a plurality of portions of the time-varying infusion schedule;
a modal average infusion rate from a set of average infusion rates for a plurality of portions of the time-varying infusion schedule;
a maximum average infusion rate from a set of average infusion rates for a plurality of portions of the time-varying infusion schedule;
a minimum infusion rate in a rate-selector table of the pump stored on the memory;
a maximum infusion rate in a rate-selector table of the pump stored on the memory;
a median infusion rate in a rate-selector table of the pump stored on the memory;
a modal infusion rate in a rate-selector table of the pump stored on the memory;

an average infusion rate in a rate-selector table of the pump stored on the memory;

an average infusion rate of an infusion history of the patient;

a minimum infusion rate of an infusion history of the patient;

a maximum infusion rate of an infusion history of the patient;

an average infusion rate for a portion of an infusion history of the patient;

a minimum average infusion rate from a set of average infusion rates for a plurality of portions of an infusion history of the patient;

a maximum average infusion rate from a set of average infusion rates for a plurality of portions of an infusion history of the patient;

a median average infusion rate from a set of average infusion rates for a plurality of portions of an infusion history of the patient; or a modal average infusion rate from a set of average infusion rates for a plurality of portions of an infusion history of the patient.

35. The method of claim 27, wherein the implantable fluid delivery device includes a processor for controlling infusion of the therapeutic agent, wherein determining the default infusion schedule is performed by the processor.

36. The method of claim 27, wherein the memory is a processor-controlled memory.

37. The method of claim 27, wherein the memory is a hardware-controlled memory.

38. The method of claim 27, wherein storing the default infusion schedule on the memory comprises:
storing a first copy of the default infusion schedule in a first portion of the memory; and
storing a second copy of the default infusion in a second portion of the memory.

39. The method of claim 38, wherein the first portion of the memory is a first type of memory and the second portion of the memory is a second type of memory.

40. The method of claim 27, further comprising storing the therapy program on the memory of the implantable fluid delivery device.

41. The method of claim 40, wherein the default infusion schedule is stored on a first portion of the memory and the therapy program is stored on a second portion of the memory.

42. The method of claim 41, wherein the second portion is a processor-controlled memory.

43. The method of claim 41, wherein the first portion of the memory comprises a first type of memory and the second portion of the memory comprises a second type of memory.

44. The method of claim 27, further comprising initiating an alarm upon determining that the error condition is present or delivering the therapeutic agent to the patient according to the default infusion schedule.

45. A non-transitory computer-readable storage medium comprising instructions for causing a programmable processor to:
determine a default infusion schedule based on a therapy program that defines delivery of a therapeutic agent to a patient by an implantable fluid delivery device;
store a default infusion schedule based on a therapy program that defines delivery of a therapeutic agent to a patient by an implantable fluid delivery device on the computer-readable medium;
determine if an error condition is present in the implantable fluid delivery device such that the device cannot continue delivering therapy according to the therapy program; and
if the error condition is present, deliver the therapeutic agent according to the default infusion schedule.

46. A fluid delivery system comprising:
means for delivering a therapeutic agent to a patient;
means for storing a therapy program defining the delivery of the therapeutic agent to the patient by the means for delivering the therapeutic agent;
means for storing a default infusion schedule based on the therapy program; and
means for controlling the means for delivering the therapeutic agent to the patient;
means for determining an error condition that prevents the means for delivering the therapeutic agent to the patient from continuing to deliver therapy according to the therapy program;
wherein the means for controlling the means for delivering the therapeutic agent to the patient directs delivery of the therapeutic agent to the patient according to the default infusion schedule when the means for determining an error condition determines that the error condition is present.

47. The system of claim 46, wherein the means for storing a therapy program comprises at least one of read-only memory (ROM), random access memory (RAM), non-volatile RAM (NVRAM), electrically erasable programmable read-only memory (EEPROM), or flash memory.

48. The system of claim 46, wherein the means for storing a default infusion schedule comprises at least one of read-only memory (ROM), random access memory (RAM), non-volatile RAM (NVRAM), electrically erasable programmable read-only memory (EEPROM), flash memory, or hardware registers.

49. The system of claim 46, wherein the therapy program comprises a therapy infusion schedule and the default infusion schedule is determined based on the therapy infusion schedule.

50. The system of claim 49, wherein the therapy infusion schedule comprises a continuous infusion rate and the default infusion schedule comprises a fixed default infusion rate equal to the continuous infusion rate of the therapy infusion schedule.

51. The system of claim 50, wherein the therapy infusion schedule comprises a time-varying infusion schedule.

52. The system of claim 51, wherein the default infusion schedule is a fixed default infusion rate that is equal to at least one of:
an average infusion rate of the time-varying infusion schedule;
a minimum infusion rate of the time-varying infusion schedule;
a maximum infusion rate of the time-varying schedule;
an average infusion rate for a portion of the time-varying infusion schedule;
a minimum average infusion rate from a set of average infusion rates for a plurality of portions of the time-varying infusion schedule;
a median average infusion rate from a set of average infusion rates for a plurality of portions of the time-varying infusion schedule;
a modal average infusion rate from a set of average infusion rates for a plurality of portions of the time-varying infusion schedule;

a maximum average infusion rate from a set of average infusion rates for a plurality of portions of the time-varying infusion schedule;
a minimum infusion rate in a rate-selector table of the pump stored on the memory;
a maximum infusion rate in a rate-selector table of the pump stored on the memory;
a median infusion rate in a rate-selector table of the pump stored on the memory;
a modal infusion rate in a rate-selector table of the pump stored on the memory;
an average infusion rate in a rate-selector table of the pump stored on the memory;
an average infusion rate of an infusion history of the patient;
a minimum infusion rate of an infusion history of the patient;
a maximum infusion rate of an infusion history of the patient;
an average infusion rate for a portion of an infusion history of the patient;
a minimum average infusion rate from a set of average infusion rates for a plurality of portions of an infusion history of the patient;
a maximum average infusion rate from a set of average infusion rates for a plurality of portions of an infusion history of the patient;
a median average infusion rate from a set of average infusion rates for a plurality of portions of an infusion history of the patient; or
a modal average infusion rate from a set of average infusion rates for a plurality of portions of an infusion history of the patient.

53. The system of claim 46, further comprising means for alarming upon determination of the error condition or delivery of the therapeutic agent to the patient according to the default infusion schedule.

* * * * *